(12) United States Patent
Hillman et al.

(10) Patent No.: US 6,171,790 B1
(45) Date of Patent: Jan. 9, 2001

(54) HUMAN PROTEASE ASSOCIATED PROTEINS

(75) Inventors: Jennifer L. Hillman, Mountain View; Y. Tom Tang, San Jose; Preeti Lal, Sunnyvale; Neil C. Corley, Mountain View; Karl J. Guegler, Menlo Park; Chandra Patterson, Mountain View, all of CA (US)

(73) Assignee: Incyte Pharmaceuticals, Inc., Palo Alto, CA (US)

( * ) Notice: Under 35 U.S.C. 154(b), the term of this patent shall be extended for 0 days.

(21) Appl. No.: 09/071,709

(22) Filed: May 1, 1998

(51) Int. Cl.$^7$ .............................. C12N 15/57; C12N 9/64; C12N 15/09
(52) U.S. Cl. .................... 435/6; 435/320.1; 435/325; 435/252.3; 435/226; 435/69.1; 536/231; 536/23.5; 536/23.2
(58) Field of Search .................... 536/23.2, 23.5, 536/23.1; 435/320.1, 252.3, 325, 226, 69.1, 6

(56) References Cited

FOREIGN PATENT DOCUMENTS

| 0 759 467 A2 | 2/1997 | (EP) . |
| 0 796 913 A2 | 9/1997 | (EP) . |
| 0 939 131 A2 | 9/1999 | (EP) . |
| 98/08866 | 3/1998 | (WO) . |

OTHER PUBLICATIONS

EMBL Accession No. H00225, Jun. 1995.*
EMBL Accession No. N73656, Jun. 1995.*
EMBL entry AA047604, Jan. 1997.*
Hayashi et al., "Endooligopeptidase A related protein", EMBL Sequence Database, Jun. 1, 1998, XP002114379, Heidelberg, DE (Accession 046480).
Andersson et al., "Homo sapiens clone 23596 mRNA sequence", EMBL Sequence Database, Jan. 21, 1998, XP002114381, Heidelberg, DE (Accession AF038203).
Andersson, B. et al., "A 'Double Adaptor' Method for Improved Shotgun Library Construction", *Anal. Biochem.*, 236 (1) :107–113 (1996).
Hillier et al., "WashU–Merck EST Project 1997", EMBL Sequence Database, Jun. 5, 1997, XP002114382, Heidelberg, DE (Accession AA442918).
Hillier et al., "WashU–NCI human EST Project", EMBL Sequence Database, Jan. 6, 1998, XP002114380, Heidelberg, DE (Accession AA716616).
Hillier et al., "WashU–Merck EST Project 1997", EMBL Sequence Database, May 5, 1997, XP002114383, Heidelberg, DE (Accession AA411180).
Denda, K., "Homo sapiens mRNA for hepatocyte growth factor activator inhibitor", EMBL Sequence Database, Mar. 10, 1998, XP002114384, Heidelberg, DE (Accession AB000095).
Shimomura et al., "Hepatocyte growth factor activator inhibitor", EMBL Sequence Database, Jun. 1, 1998, XP002114385, Heidelberg, DE (Accession O43278).
"P27; mRNA sequence", EMBL Sequence Database, Mar. 30, 1998, XP002114387, Heidelberg, DE (Accession AA883244).
Hillier et al., "WashU–NCI human EST Project", EMBL Sequence Database, May 1, 1997, XP002114388, Heidelberg, DE (Accession AA402156).
Hillier et al., "WashU–NCI human EST Project", EMBL Sequence Database, May 1, 1997, XP002114389, Heidelberg, DE (Accession AA402037).
Wilk et al., "Homo sapiens aspartyl aminopeptidase mRNA", EMBL Sequence Database, Jan. 6, 1999, XP002114390, Heidelberg, DE (Accession AF005050).

* cited by examiner

Primary Examiner—Rebecca E. Prouty
(74) Attorney, Agent, or Firm—Incyte Genomics, Inc.

(57) ABSTRACT

The invention provides human protease associated proteins (HPRAP) and polynucleotides which identify and encode HPRAP. The invention also provides expression vectors, host cells, antibodies, agonists, and antagonists. The invention also provides methods for diagnosing, treating or preventing disorders associated with expression of HPRAP.

15 Claims, 30 Drawing Sheets

```
                  11          20          29          38          47          56
5' CGGGC GCG GAG GTA CGC TGA GTG GAG CTC GGG GCT GCG TAG GGG AGC TGA GCC GAG 65          74          83          92         101         110
   CGG CTG GGC GGG CCT GGC CGG GCC AGC GGA GGG GAG ACG TCG GTT GAG CGG CGG 119         128         137         146         155         164
   CGA ACA TGC GCT TTT GAC ACA TTG GAG GCT TTC TTG ATC ATG GAT GGT GAA GAT
                                                       M   D   G   E   D 173         182         191         200         209         218
   ATA CCA GAT TTT TCA AGT TTA AAG GAG GAA ACT GCT TAT TGG AAG GAA CTT TCC
    I   P   D   F   S   S   L   K   E   E   T   A   Y   W   K   E   L   S 227         236         245         254         263         272
   TTG AAG TAT AAG CAA AGC TTC CAG GAA GCA GAT GAG CTA GTT GAA TTC CAG
    L   K   Y   K   Q   S   F   Q   E   A   D   E   L   V   E   F   Q 281         290         299         308         317         326
   GAA GGA AGC AGA GAA GAG TTG GAG GCA CAA TTA GAG GTA CAG GCT GAA
    E   G   S   R   E   E   L   E   A   Q   L   E   V   Q   A   E 335         344         353         362         371         380
   CAA AGA AAT AGA GAC TTG CAG GCT GAT AAC CAA AGA CTG AAA TAT GAA GTG GAG
    Q   R   N   R   D   L   Q   A   D   N   Q   R   L   K   Y   E   V   E

FIGURE1A
```

```
        389            398      407       416      425       434
GCA TTA AAG GAG AAG CTA GAG CAT CAA TAT GCA CAG AGC TAT AAG CAG GTC TCA
 A   L   K   E   K   L   E   H   Q   Y   A   Q   S   Y   K   Q   V   S 443            452      461       470      479       488
GTG TTA GAA GAT GAT TTA AGT CAG ACT CGG GCC ATT AAG GAG CAG TTG CAT AAG
 V   L   E   D   D   L   S   Q   T   R   A   I   K   E   Q   L   H   K 497            506      515       524      533       542
TAT GTG AGA GAG CTG GAG CAG GCC AAC GAC GAC CTG AAA AGG CGA GTT CAT GCA
 Y   V   R   E   L   E   Q   A   N   D   D   L   K   R   R   V   H   A 551            560      569       578      587       596
ACA ATA GTT TCA CTG GAA GAC TTT GAA CAA AGG CTA AAC CAG GCC ATT GAA CGA
 T   I   V   S   L   E   D   F   E   Q   R   L   N   Q   A   I   E   R 605            614      623       632      641       650
AAT GCA TTT TTA GAA AGT GAA CTT GAT GAA AAG GAA TCT TTG GTC TCT GTA
 N   A   F   L   E   S   E   L   D   E   K   E   S   L   V   S   V 659            668      677       686      695       704
CAG AGG TTA AAG GAT GAA GCA AGA GAT TTA AGG CAA GAA CTA GCA GTT CGG GAA
 Q   R   L   K   D   E   A   R   D   L   R   Q   E   L   A   V   R   E 713            722      731       740      749       758
AGA CAA CAG GAA GTA ACT AGA AAG TCG GCT CCT AGC TCT CCA ACT CTA GAC TGT
 R   Q   Q   E   V   T   R   K   S   A   P   S   S   P   T   L   D   C
```

FIGURE 1B

```
     767          776          785          794          803          812
GAA AAG ATG GAC TCC GCC GTC CAA TCA CTT TCT TTG CCA GCT ACC CCT GTT
 E   K   M   D   S   A   V   Q   S   L   S   L   P   A   T   P   V 821          830          839          848          857          866
GGC AAA GGA ACG GAG AAC ACT TTT CCT TCA CCG AAA GCT ATA CCA AAT GGT TTT
 G   K   G   T   E   N   T   F   P   S   P   K   A   I   P   N   G   F 875          884          893          902          911          920
GGT ACC AGT CCA CTA ACT CCC TCT GCT AGG ATA TCA GCA CTA AAC ATC GTG GGG
 G   T   S   P   L   T   P   S   A   R   I   S   A   L   N   I   V   G 929          938          947          956          965          974
GAT CTC TTA CGG AAA GTA GGG GCT TTA GAA TCC TAT ATT TCA GCA TGC AGG AAT
 D   L   L   R   K   V   G   A   L   E   S   Y   I   S   A   C   R   N 983          992          1001         1010         1019         1028
TTT GCA AAG GAC CAA GCA TCA CGA AAA TCC AAA GTT AAC TGT
 F   A   K   D   Q   A   S   R   K   S   K   Y   I   S   G   N   V   C 1037         1046         1055         1064         1073         1082
GGG GTG CTG AAT GGC ACA AAG TTC TCT CGA TCA GGG CAT ACA TCT TTC
 G   V   L   N   G   T   K   F   S   R   S   G   H   T   S   F 1091         1100         1109         1118         1127         1136
TTC GAC AAA GGG GCA GTA AAC GGC TTT GAC CCC GCT CCT CCT CCT GGT CTG
 F   D   K   G   A   V   N   G   F   D   P   A   P   P   P   G   L
```

FIGURE 1C

```
1145              1154              1163              1172              1181              1190
GGC TCC TCG CGT CCA TCA GCG CCG GGT ATG CTG CCT CTC AGT GTG CGA GTG
 G   S   S   R   P   S   A   P   G   M   L   P   L   S   V   R   V 1199              1208              1217              1226              1235              1244
CCT AGC CTC CAG GTG GGG GCT CCT GCC CTC CTC CAA CAA CCC AGG ACA CCC ACG
 P   S   L   Q   V   G   A   P   A   L   L   Q   Q   P   R   T   P   T 1253              1262              1271              1280              1289              1298
CCT CAC CCC TCG GTG CCT GGG AGC CCC GTG CCC CTC CGT CTG CCT CCG CAC
 P   H   P   S   V   P   G   S   P   V   P   L   R   L   P   P   H 1307              1316              1325              1334              1343              1352
GGC CAG AGG GCA GGC TGC ATG CAG TGG CGG CTA CTG GGC CCT GCC CAG CCC
 G   Q   R   A   G   C   M   Q   W   R   L   L   G   P   A   Q   P 1361              1370              1379              1388              1397              1406
CGG AAC TCT GCG CGA TAT CAA TAC TGG CTA TTT TCT CTT GCC GTA GTG CCG
 R   N   S   A   R   Y   Q   Y   W   L   F   S   L   A   V   V   P 1415              1424              1433              1442              1451              1460
TTG GTT TCA CAT GAT TGC ACT TTT GTG GGT CGC AAG GTG ATA CAT ACG TGT ATT
 L   V   S   H   D   C   T   F   V   G   R   K   V   I   H   T   C   I 1469              1478              1487              1496              1505              1514
ACT TGG TCA CTG GAT GCA GAA GTA CCC ATT CAT CAC ACC TGC CCC ATA GCC CCC
 T   W   S   L   D   A   E   V   P   I   H   H   T   C   P   I   A   P
```

FIGURE 1D

```
      1523           1532           1541           1550           1559           1568
ACT CTG CTG TAC TGA TAG GAT TTA GTT GTG TTT TAG GAC ATT GCA AAT CTT CTA
 T   L   L   Y 1577           1586           1595           1604           1613           1622
GAA GTT CTC CCC CAA ATC AGG TCA ATG TGT GCC CTC CTG AGC TCC CAC CCA GGC 1631           1640           1649           1658           1667           1676
ATC TCC AGT GCT CAT GAT CAT GTG TCC CCC AAC TCC ACC CCT CAC AGT TTG GGC 1685           1694           1703           1712           1721           1730
CTG TTT CTG GCA AAG AGT CAG GAA GGT TAC TGA ATT AGG GAA CAT TTT CTG CAC 1739           1748           1757           1766           1775           1784
CTT CTG ATT TTA CTT AAG CAG CTA CCA TTC CAT GGA CTT GCC TCC CAG AGC AGC 1793           1802           1811           1820           1829           1838
ACA ATG CCC GTC TGA GCC CCA CGT GGC AGG AGC CTC TGG GAC GGG GCA CAC ACA 1847           1856           1865           1874           1883           1892
GGC CCA GCC TCT GTG CTG TCT CCT CCT CTG TGC GCC TCA GAC TCG GGG TGA GGG 1901           1910           1919           1928           1937           1946
AGG CGG GCA GCC TCT CGC CAG CCT TCC CGT CCT TCA GTT CAA CGA CAT CTT TGG
```

FIGURE 1E

```
                1955           1964           1973           1982           1991           2000
           AGT GTT TTT GTT TTC TCT TCC AAG CGT CCC GTT GTG TTA GGA AGG GTG AGT 2009           2018           2027           2036           2045           2054
           GGC TGG TTC CAG GGT GGG CCG GTG CCA GCT CCG GGG TGG ACT GAA CAG CGG CGG
            G   W   F   Q   G   G   P   V   P   A   P   G   W   T   E   Q   R   R 2063           2072           2081           2090           2099           2108
           CTG TCC CTG TGC ATC CTT TGA TTA CTC TCA TGC TGC ATT TAC TGT TTA CAT TTG 2117           2126           2135           2144           2153           2162
           TTT TAT TGT ACA TAG GTT TGT AAA CAT TAT TGC CTG AGA TAT TTG TAT ATA ACT 2171           2180           2189           2198           2207           2216
           TGG GCT TTG TAG CTT TTA TTT ATT CAG AAC GCA TAC GGC ATG TTA ATG ACT CTG 2225           2234           2243           2252           2261           2270
           ATG GTG TCC TCC TCT GGG CAG CTG TAT AGG ATC ATC ATG TGG TTA CAA AAA ATA 2279           2288           2297           2306           2315           2324
           CTT CCC TCA AAA AAA TTC TTT TAA TGT GGA AAC AAT AAA TTT CAC AGA AAA AAA

AAA  3'
```

FIGURE 1F

```
                       10           19           28           37           46           55
5' CTGA GAG AAG CCT GGT CCA TCT AGT GAG AAT TGA CCT TAT CTC ACT TTC TCT CCC 64           73           82           91          100          109
   CGC CAG GGT CTG GGA TCC CCA AGG CAG ACT GCA TAG ACT TGA AGG TAC AAC 118          127          136          145          154          163
   CCC AGG AAC CCC TGG TGC TGA AGG ATG TGG AAA ACA CAG ATT GGC GCC TAC TGC
                                     M   W   K   T   Q   I   G   A   Y   C 172          181          190          199          208          217
   GGG GTG ACA ACG GAT GTC AGG GTA GAG AGG AAA GAC CCA AAC CAG GTG GAA CTG
    G   V   T   T   D   V   R   V   E   R   K   D   P   N   Q   V   E   L 226          235          244          253          262          271
   TGG GGA CTC AAG GAA GGC ACC TAC TTC CAG CTG TTC CAG ACA CTG ACA AGC TCA GAC
    W   G   L   K   E   G   T   Y   F   Q   L   F   Q   T   L   T   S   S   D 280          289          298          307          316          325
   CAC CCA GAG GAC ACG GCC AAC GTC ACT GTG CTG TCC ACC AAG CAG ACA
    H   P   E   D   T   A   N   V   T   V   L   S   T   K   Q   T 334          343          352          361          370          379
   GAA GAC TAC TGC CTC GCA TCC AAC AAG GTG GGT CGC TGC CGG GGC TCT TTC
    E   D   Y   C   L   A   S   N   K   V   G   R   C   R   G   S   F
```

```
                388                 397                 406                 415                 424                 433
CCG CGC TGG TAC TAT GAC CCC ACG GAG CAG ATC TGC AAG AGT TTC GTT TAT GGA
 P   R   W   Y   Y   D   P   T   E   Q   I   C   K   S   F   V   Y   G 442                 451                 460                 469                 478                 487
GGC TGC TTG GGC AAC AAG AAC CTT CGG GAA GAG GAG TGC ATT CTA GCC
 G   C   L   G   N   K   N   L   R   E   E   E   C   I   L   A 496                 505                 514                 523                 532                 541
TGT CGG GGT GTG CAA GGG CCT TTG AGA GGC AGC TCT GGG GCT CAG GCG ACT
 C   R   G   V   Q   G   P   L   R   G   S   S   G   A   Q   A   T 550                 559                 568                 577                 586                 595
TTC CCC CAG GGC CCC ATG GAA TTG AGA AGG CGC CAT CCA GTG TCT GGC ACC TGT
 F   P   Q   G   P   M   E   L   R   R   R   H   P   V   S   G   T   C 604                 613                 622                 631                 640                 649
CAG CCC ACC CAG TTC CGC TGC AGC AAT GGC TGC ATC GAC GAG TTC CTG GAG
 Q   P   T   Q   F   R   C   S   N   G   C   I   D   E   F   L   E 658                 667                 676                 685                 694                 703
TGT GAC GAC ACC CCC AAC TGC CCC GAC GCC TCC GAC GAG GCT GCC TGT GAA AAA
 C   D   D   T   P   N   C   P   D   A   S   D   E   A   A   C   E   K 712                 721                 730                 739                 748                 757
TAC ACG AGT GGC TTT GAC GAG CTC CAG CGC ATC CAT TTC CCC AGT GAC AAA GGG
 Y   T   S   G   F   D   E   L   Q   R   I   H   F   P   S   D   K   G
```

```
766       775       784       793       802       811
CAC TGC GTG GAC CTG CCA GAC ACA GGA CTC TGC AAG GAG AGC ATC CCG CGC TGG
 H   C   V   D   L   P   D   T   G   L   C   K   E   S   I   P   R   W 820       829       838       847       856       865
TAC TAC AAC CCC TTC AGC GAA CAC TGC GCC CGC TTT ACC TAT GGT TGT TAT
 Y   Y   N   P   F   S   E   H   C   A   R   F   T   Y   G   C   Y 874       883       892       901       910       919
GGC AAC AAG AAC TTT GAG GAG CAG TGC CTC GAG TCT TGT CGC GGC
 G   N   K   N   F   E   E   Q   C   L   E   S   C   R   G 928       937       946       955       964       973
ATC TCC AAG GAT GTG TTT GGC CTG AGG CGG GAA ATC CCC ATT CCC AGC ACA
 I   S   K   D   V   F   G   L   R   R   E   I   P   I   P   S   T 982       991       1000      1009      1018      1027
GGC TCT GTG GAG ATG GCT GTC GCA GTG TTC CTG GTC ATC TGC ATT GTG GTG
 G   S   V   E   M   A   V   A   V   F   L   V   I   C   I   V   V 1036      1045      1054      1063      1072      1081
GTA GCC ATC TTG GGT TAC TGC TTC TTC AAG AAC CAG AGA AAG GAC TTC CAC GGA
 V   A   I   L   G   Y   C   F   F   K   N   Q   R   K   D   F   H   G 1090      1099      1108      1117      1126      1135
CAC CAC CAC CAC CCA CCT GCC CCT ACC CCC AGC TCC ACT GTC TCC ACT ACC GAG
 H   H   H   H   P   P   A   P   T   P   S   S   T   V   S   T   T   E
```

FIGURE2C

```
     1144           1153           1162           1171           1180           1189
GAC ACG GAG CAC CTG GTC TAT AAC CAC ACC ACC CGG CCC CTC TGA GCC TGG GTC
 D   T   E   H   L   V   Y   N   H   T   T   R   P   L 1198           1207           1216           1225           1234           1243
TCA CCG GCT CTC ACC TGG CCC TGC TTC CTG CTT GCC AAG GCA GAG GCC TGG GCT 1252           1261           1270           1279           1288           1297
GGG AAA AAC TTT GGA ACC AGA CTC TTG CCT GTT TCC CAG GCC CAC TGT GCC TCA 1306           1315           1324           1333           1342           1351
GAG ACC AGG GCT CCA GCC CCT CTT GGA GAA GTC TCA GCT AAG CTC ACG TCC TGA 1360           1369           1378           1387           1396           1405
GAA AGC TCA AAG GTT TGG AAG GAG CAG AAA ACC CTT GGG CCA GAA GTA CCA GAC 1414           1423           1432           1441           1450           1459
TAG ATG GAC CTG CCT GCA TAG GAG TTT GGA GGA AGT TGG AGT TTT GTT TCC TCT 1468           1477           1486           1495           1504           1513
GTT CAA AGC TGC CTG TCC CTA CCC CAT GGT GCT AGG AAG AGG AGT GGG GTG GTG
```

FIGURE 2D

```
     1522           1531           1540           1549           1558           1567
TCA GAC CCT GGA GGC CCC AAC CCT GTC CTC CCG AGC TCC TCT TCC ATG CTG TGC 1576           1585           1594           1603           1612           1621
GCC CAG GGC TGG GAG GAA GGA CTT CCC TGT GTA GTT TGT GCT GTA AAG AGT TGC 1630           1639           1648           1657           1666           1675
TTT TTG TTT ATT TAA TGC TGT GGC ATG GGT GAA GAG GAG GGG AAG AGG CCT GTT 1684           1693           1702           1711           1720           1729
TGG CCT CTC TGT CCT CTC TTC CCC CAA GAT TGA GCT CTC TGC CCT TGA 1738           1747           1756           1765           1774           1783
TCA GCC CCA CCC TGG CCT AGA CCA GCA GAC AGA GCC AGG AGA GGC TCA GCT GCA 1792           1801           1810           1819           1828           1837
TTC CGC AGC CCC CAC CCC CAA GGT TCT CCA ACA TCA CAG CCC AGC CCA CCC ACT 1846           1855           1864
GGG TAA TAA AAG TGG TTT GTG GAA AAA AAA AAA  3'
```

FIGURE 2E

```
                    10              19          28              37              46              55
5' GTTT TGG CGC ATG GGC GGA GCG TAG TTA CGG TCG ACT GGG GCG TCG TCC CTA GCC 64              73              82              91              100             109
   CGG GAG CCG GGT CTC TGG AGT CGC GGC CCG GGG TTC ACG ATG TCC GAC GAG GAA
                                                            M   S   D   E   E 118             127             136             145             154             163
   GCG AGG CAG AGC GGA GGC TCC TCG CAG GCC GGC GTG ACT GTC AGC GAC GTC
   A   R   Q   S   G   G   S   S   Q   A   G   V   T   V   S   D   V 172             181             190             199             208             217
   CAG GAG CTG ATG CGG CGC AAG GAG ATA GAA GCG CAG ATC AAG GCC AAC TAT
   Q   E   L   M   R   R   K   E   I   E   A   Q   I   K   A   N   Y 226             235             244             253             262             271
   GAC GTG CTG GAA AGC CAA AAA GGC ATT GGG ATG AAC GAG CCG CTG GTG GAC TGT
   D   V   L   E   S   Q   K   G   I   G   M   N   E   P   L   V   D   C 280             289             298             307             316             325
   GAG GGC TAC CCC CGG TCA GAC GTG TAC CAA GTC CGC ACC GCC AGG CAC
   E   G   Y   P   R   S   D   V   Y   Q   V   R   T   A   R   H 334             343             352             361             370             379
   AAC ATC ATA TGC CTG CAG AAT GAT CAC AAG GCA GTG ATG AAG CAG GTG GAG GAG
   N   I   I   C   L   Q   N   D   H   K   A   V   M   K   Q   V   E   E
```

```
388              397              406              415              424              433
GCC CTG CAC      CAG CTG CAC      GCT CGC GAC      AAG GAG CAG      GCC CGG GAC      ATG GCT
 A   L   H        Q   L   H        A   R   D        K   E   Q        A   R   D        M   A 442              451              460              469              478              487
GAG GCC CAC      AAA GAG GCC      ATG AGC CGC      AAA CTG GGT      CAG AGT GAG      AGC CAG GGC
 E   A   H        K   E   A        M   S   R        K   L   G        Q   S   E        S   Q   G 496              505              514              523              532              541
CCT CCA CGG      GCC TTC GCC      AAA GTG AAC      AGC ATC AGC      CCC GGC TCC      CCA GCC AGC
 P   P   R        A   F   A        K   V   N        S   I   S        P   G   S        P   A   S 550              559              568              577              586              595
ATC GCG GGT      AAT CCA GGG      GTT GGC CAC      TCA AGT CCA      TGC CCA AGT      GAC ACG GGT
 I   A   G        N   P   G        V   G   H        S   S   P        C   P   S        D   T   G 604              613              622              631              640              649
CTG CAA GTG      GAT GAT GAG      ATT GTG GAG      TTC GGC TCT      GTG AAC ACC      CAG AAC TTC
 L   Q   V        D   D   E        I   V   E        F   G   S        V   N   T        Q   N   F 658              667              676              685              694              703
CAG TCA CTG      CAT AAC ATT      GGC AGT GAG      CAC AGT GAG      CAG CTT AGA      GGG AAG CCC CTG
 Q   S   L        H   N   I        G   S   E        H   S   E        Q   L   R        G   K   P   L 712              721              730              739              748              757
AAT GTG ACA      GTG ATC CGC      AGG GGG GGA      AAA CAC CAG      CTT AGA CTT      GTT CCA ACA
 N   V   T        V   I   R        R   G   G        K   H   Q        L   R   L        V   P   T
```

```
      766          775          784          793          802          811
CGC TGG GCA GGA AAA GGA CTG CTG GGC TGC AAC ATT ATT CCT CTG CAA AGA TGA
 R   W   A   G   K   G   L   L   G   C   N   I   I   P   L   Q   R   *

820          829          838          847          856          865
TTG TCC CTG GGG AAC AGT AAC AGG AAA GCA TCT TCC CTT GCC CTG GAC TTG GGT 874          883          892          901          910          919
CTA GGG ATT TCC AAC TTG TCT CTC CCT GAA GCA TAA GGA TCT GGA AGA GGC 928          937          946          955          964          973
TTG TAA CCT GAA CTT CTG TGT GGT GGC AGT ACT GTG GCC CAC CAG TGT AAT CTC 982          991          1000         1009         1018         1027
CCT GGA TTA AGG CAT TCT TAA AAA CTT AGG CTT GGC CTC TTT CAC AAA TTA GGC 1036         1045         1054         1063         1072         1081
CAC GGC CCT AAA TAG GAA TTC CCT GGA TTG TGG GCA AGT GGG CGG AAG TTA TTC 1090         1099         1108         1117         1126         1135
TGG CAG GTA CTG GTG TGA TTA TTA TTT TTA ATA AAG AGT TTT ACA GTG

CTG  3'
```

```
                10        19              28              37              46              55
5' CGAG        CCC       GGA GGC CAG     ATG AGC GGA     CAC AGC CCC     ACG CGC GGG     GCC ATG CAG GTA 64              73              82              91              100      109
   AGT GGC TCC CGA CGG   CCC CAA GCT     TCC GGG TAG     CGC GGT GCA     GTG GGG CCG     CCT GAC CCA     AAG CCG GCG     CCC 118             127             136             145             154             163
   TCC GGG                GCC CAA GCT     TAG CGC GGT    GCA GTG GGG     CCG CCT GAC     CCA AAG CCG    GCG CCC 172             181             190             199             208             217
   AAC CGA AAG            CCC CGC GGA     GGG TGA CCT    GAC GAC TTT     CCC GGG ACT    GGA AGG GGG 226             235             244             253             262             271
   AGT CCT GCG            AGA GAC TAG    GTG GCC ATG    AAC GGT AAG    GCC CGC CGG    AAA GAG GCG GTG
                                                         M   N   G      K   A   R       K   E   A   V 280             289             298             307             316             325
   CAG ACT GCG            GCT AAG GAA    CTC CTC TTC    GTG AAG TTC    GTG AAC CGG    AGT CCC TCT CCT TTC
    Q   T   A              A   K   E      L   L   F      V   K   F      V   N   R      S   P   S   P   F 334             343             352             361             370             379
   CAT GCT GTG            GCT GAA TGC    GAA CGC AAC    CGC CTT CTC    CAG GCT GGC    TTC AGT GAA CTC
    H   A   V              A   E   C      E   R   N      R   L   L      Q   A   G      F   S   E   L
```

FIGURE 4A

```
                388           397           406           415           424           433
AAG GAG ACT GAG AAA ATT AAG CCC GAG AGC AAG TAC TTC ATG ACC AGG
 K   E   T   E   K   I   K   P   E   S   K   Y   F   M   T   R 442           451           460           469           478           487
AAC TCC ACC ATC ATA GCT TTT GCT GTA GGG GGC CAG TAC GTT CCT GGC AAT
 N   S   T   I   I   A   F   A   V   G   G   Q   Y   V   P   G   N 496           505           514           523           532           541
GGC TTC AGC CTC ATC GGG GCC CAC ACG GAC AGC CCC TGC CTC GGT GTG AAA CGT
 G   F   S   L   I   G   A   H   T   D   S   P   C   L   G   V   K   R 550           559           568           577           586           595
CGG TCT CGC AGC CAG GTG GGC TTC CAG CAA GTC GGT GTG GAG ACC TAT GGT
 R   S   R   S   Q   V   G   F   Q   Q   V   G   V   E   T   Y   G 604           613           622           631           640           649
GGT GGG ATC TGG AGC ACC TCA GGT TTT GAC CGT GAC CTG ACT CTG GCT GGA CGC GTC
 G   G   I   W   S   T   S   G   F   D   R   D   L   T   L   A   G   R   V 658           667           676           685           694           703
AAG TGC CCT ACC ATC CCA CAC CTG CGG CTG GAG CAG CAG CAG CTG GTG CAC GTG GAG
 K   C   P   T   I   P   H   L   R   L   E   Q   Q   Q   L   V   H   V   E 712           721           730           739           748           757
ATT GTC ATT CTT CGC ATC CCA CAC CTG GCC ATC CAT CTG CAG CGA AAT ATC AAC
 I   V   I   L   R   I   P   H   L   A   I   H   L   Q   R   N   I   N
```

FIGURE 4B

```
GAG AAC TTT GGG CCC AAC ACA GAG ATG CAT CTA GTC CCC ATT CTT GCC ACA GCC
 E   N   F   G   P   N   T   E   M   H   L   V   P   I   L   A   T   A
766         775         784         793         802         811

ATC CAG GAG GAG CTG GAG AAG GGG ACT CCT GAG CCA GGG CCT CTC AAT GCT GTG
 I   Q   E   E   L   E   K   G   T   P   E   P   G   P   L   N   A   V
820         829         838         847         856         865

GAT GAG CGG CAC CAT TCG GTC CTC ATG TCC ATG CTC TGT GCC CAT CTG GGG CTG
 D   E   R   H   H   S   V   L   M   S   M   L   C   A   H   L   G   L
874         883         892         901         910         919

AGC CCC AAG GAC ATA GTG GAG ATG GAG CTC TGC CTT GCA GAC ACC CAG CCT GCG
 S   P   K   D   I   V   E   M   E   L   C   L   A   D   T   Q   P   A
928         937         946         955         964         973

GTC TTG GGT GCC TAT GAT GAG TTC ATC TTT GCT CCT CGG CTG GAC AAT CTG
 V   L   G   A   Y   D   E   F   I   F   A   P   R   L   D   N   L
982         991         1000        1009        1018        1027

CAC AGC TGC TTC TGT GCC CTG CAG GCC TTG ATA GAT TCC TGT GCA GGC CCT GGC
 H   S   C   F   C   A   L   Q   A   L   I   D   S   C   A   G   P   G
1036        1045        1054        1063        1072        1081

TCC CTG GCC ACA GAG CCT CAC GTG CGC ATG GTC ACA CTC TAT GAC AAC GAA GAG
 S   L   A   T   E   P   H   V   R   M   V   T   L   Y   D   N   E   E
1090        1099        1108        1117        1126        1135
```

FIGURE 4C

```
1144           1153           1162           1171           1180           1189
GTG GGG TCT GAG AGT GCA CAG GGA GCA CAG TCA CTG ACA GAG CTG GTG CTG
 V   G   S   E   S   A   Q   G   A   Q   S   L   T   E   L   V   L 1198           1207           1216           1225           1234           1243
CGG CGG ATC TCA GCC TCG TGC CAG CAC CCG ACA GCC TTC GAG GAA GCC ATA CCC
 R   R   I   S   A   S   C   Q   H   P   T   A   F   E   E   A   I   P 1252           1261           1270           1279           1288           1297
AAG TCC TTC ATG ATC AGC GCA GAC ATG GCC CAT GCT GTG CAT CCC AAC TAC CTG
 K   S   F   M   I   S   A   D   M   A   H   A   V   H   P   N   Y   L 1306           1315           1324           1333           1342           1351
GAC AAG CAT GAG GAG AAC CAC CGG CCT TTA TTC CAC AAG GGC CCC GTG ATC AAG
 D   K   H   E   E   N   H   R   P   L   F   H   K   G   P   V   I   K 1360           1369           1378           1387           1396           1405
GTG AAC AGC AAG CAA CGC TAT GCT TCA AAC GCG GTG TCA GAG GCC CTG ATC CGA
 V   N   S   K   Q   R   Y   A   S   N   A   V   S   E   A   L   I   R 1414           1423           1432           1441           1450           1459
GAG GTG GCC AAC AAA GTC AAG GTC CCC CTG CAG GAT CTC ATG GTC CGG AAT GAC
 E   V   A   N   K   V   K   V   P   L   Q   D   L   M   V   R   N   D 1468           1477           1486           1495           1504           1513
ACC CCC TGT GGA ACC ACC ATT GGA CCT ATC TTG GCT TCT CGG GGG CTG CGG
 T   P   C   G   T   T   I   G   P   I   L   A   S   R   L   G   L   R
```

FIGURE 4D

```
        1522              1531              1540              1549              1558              1567
GTG CTG GAT TTA GGC AGC CCC CAA CTG GCC ATG CAC TCT ATC CGG GAG ATG GCC
 V   L   D   L   G   S   P   Q   L   A   M   H   S   I   R   E   M   A 1576              1585              1594              1603              1612              1621
TGC ACC ACA GGA GTC CTC CAG ACC CTC ACC CTC TTC AAG GGC TTC TTT GAG CTG
 C   T   T   G   V   L   Q   T   L   T   L   F   K   G   F   F   E   L 1630              1639              1648              1657              1666              1675
TTC CCT TCT CTA AGC CAT AAT CTC TTA GTG GAT TGA GCC CTC TTG GAA AGA CTT
 F   P   S   L   S   H   N   L   L   V   D 1684              1693              1702              1711              1720              1729
CTC TGC CAT CCC TTT GCA CCT GAG AGG GGA AGT TCT CAG CTG AGC TGA AGC TGG 1738              1747              1756              1765              1774              1783
ATT ATT AAA GTG GAT TGT CAC TCA GAC TCT CCG TGC TAC GCT TAT TTG GAG ACT 1792              1801              1810              1819              1828              1837
AGA GGA GTG GGA GTT GAG CCT GGC TTG AAC CTT TGG AAC CAG AAA AGT TGG GGA 1846              1855              1864              1873              1882              1891
GCA GGT GGA GGA GGC CAC ACT CCT GGG AGC TGA TGG TTT TAA ATC TGG TTT TAA 1900              1909
ATC TCA AAA AAA AAA AAA A 3'
```

FIGURE 4E

```
1    -------------------------------------- 031381
1    KPACSSVRLTTREKPHCVCQDPMTCPPAKL         GI 2827886

1    -------------------------------------- 031381
31   LDQVCGTDNQTYTSSCYLFATKCKLEGTKK         GI 2827886

1    -------------------------------------- 031381
61   GHQLQLITWSLQIYPACTDFEVTQFPLRMR         GI 2827886

1    -------------------------------------- 031381
91   DWLKNISCSCMNLTLNTLDISTRSRETKSR         GI 2827886

1    -------------------------------------- 031381
121  KSTWMKKRLLAGDHPIDLLLREHRATSRFG         GI 2827886

1    -------------------------------------- 031381
151  QVRQLLTCRGGAGCRGARSGAQGCGGNGAE         GI 2827886

1    -------------------------------------- 031381
181  RLGRPGQASGAEASVSRRRTCAFDTLEAFL         GI 2827886
```

FIGURE 5A

|     |                                                              |             |
| --- | ------------------------------------------------------------ | ----------- |
| 1   | -MDGEDIPDFSSLKEETAYWKELSLKYKQS                               | 031381      |
| 211 | IMDGEDIPDFSSLKEETAYWKELSLKYKQS                               | GI 2827886  |
| 30  | FQEARDELVEFQEGSRELEAELEAQLVQAE                               | 031381      |
| 241 | SRKARDELVEFQEGSRELEAELEAQLVQAE                               | GI 2827886  |
| 60  | QRNRDLQADNQRLKYEVEALKEKLEHQYAQ                               | 031381      |
| 271 | QRNRDLQADNQRLKYEVEALKEKLEHQYAQ                               | GI 2827886  |
| 90  | SYKQVSVLEDDLSQTRAIKEQLHKYVRELE                               | 031381      |
| 301 | SYKQVSVLEDDLSQTRAIKEQLHSTCRELE                               | GI 2827886  |
| 120 | QANDDLERAKRATIVSLEDFQRLNQAIER                                | 031381      |
| 331 | QANDDLERAKRATIVSLETLT-KLNQAIER                               | GI 2827886  |
| 150 | NAFLESELDEKESLLVSVQRLKDEARDLRQ                               | 031381      |
| 360 | NAFLESELDEKESLLVSVQRLKDEARDLRQ                               | GI 2827886  |
| 180 | ELAVRERQQEVTRKSAPSSPTLDCEKMDSA                               | 031381      |
| 390 | ELAVRERQQEVTRKSAPSSPTLDCEKMDSA                               | GI 2827886  |

FIGURE 5B

| | | |
|---|---|---|
| 210 | V Q A S L S L P A T P V G K G T E N T F P S P K A I P N G F | 031381 |
| 420 | V Q A S L S L P A T P V G K G T E N S F P S P K A I P N G F | GI 2827886 |
| 240 | G T S P L T P S A R I S A L N I V G D L L R K V G A L E S K | 031381 |
| 450 | G T S P L T P S A R I S A L N I V G D L L R K V G A L E S K | GI 2827886 |
| 270 | L A A C R N F A K D Q A S R K S Y I S G N V N C G V L N G N | 031381 |
| 480 | L A A C R N F A K D Q A S R K S Y I S G N V N C G V M N S N | GI 2827886 |
| 300 | G T K F S R S G H T S F F D K G A V N G F D P A P P P P G L | 031381 |
| 510 | G T K F S R S G H T S F F D K G A V N G F D P A P P P P G L | GI 2827886 |
| 330 | G S S R P S S A P G M L P L S V R V P S L Q V G A P A L L Q | 031381 |
| 540 | G S S R P L S A P G M C R S V C E C P A - - S G A P A L L Q | GI 2827886 |
| 360 | Q P R T P T P H P S V P G P S P V P L R L P P H G W Q R A G | 031381 |
| 568 | Q P R T P T P H P S V P G P A L C P P S A S P H G W Q R A G | GI 2827886 |

```
208  GHCVDLPDTGLCKESIPRWYYNPFSEHCAR    1319265
132  -YCTANAVTGPCRASFPRWYFDVERNSCNN    GI 2065529

238  FTYGGCYGNKNNFEEQQCLESCRGISKKD     1319265
161  FIYGGCRGNKNSYRSEEACMLRC-----      GI 2065529

268  VFGLRREIPIPSTGSVEMAVAFLVICIVV     1319265
184  -FRQQENPPLPLGSKVVVLAGLFVMVLILF    GI 2065529

298  VVAILGYCFFKNQRKDFHGHHHHPPPTPAS    1319265
213  LGASMVY-LIRVARRN------QERAL       GI 2065529

328  STV-STTEDTEHLVYNHTTRPL            1319265
233  RTVWSSGDDKEQLV--KNTYVL            GI 2065529
```

FIGURE 6B

|  |  |  |
|---|---|---|
| 1 | MSDEEARQSGGSSQAGAVTVSDVQELMRRK | 2057812 |
| 1 | MSDEEARQSGGSSQAGVVTVSDVQELMRRK | GI 2055256 |
| 31 | EEIEAQIKANYDVLESQKGIGMNEPLVDCE | 2057812 |
| 31 | EEIEAQIKANYDVLESQKGIGMNEPLVDCE | GI 2055256 |
| 61 | GYPRSDVDLYQVRTARHNIICLQNDHKAVM | 2057812 |
| 61 | GYPRSDVDLYQVRTARHNIICLQNDHKAVM | GI 2055256 |
| 91 | KQVEEALHQLHARDKEKQARDMAEAHKEAM | 2057812 |
| 91 | KQVEEALHQLHARDKEKQARDMAEAHKEAM | GI 2055256 |
| 121 | SRKLGQSESQGPPRAFAKVNSISPGSPASI | 2057812 |
| 121 | SRKLGQSESQGPPRAFAKVNSISPGSPASI | GI 2055256 |

FIGURE 7A

| | | | |
|---|---|---|---|
| 151 | A G N P G V G H S S P C P G D T G L Q V D D E I V E F G S V | 2057812 |
| 151 | A G - - - - - - - - - - - - - - L Q V D D E I V E F G S V | GI 2055256 |
| 181 | N T Q N F Q S L H N I G S V V Q H S E G K P L N V T V I R R | 2057812 |
| 166 | N T Q N F Q S L H N I G S V V Q H S E G - A L A P T I L L S | GI 2055256 |
| 211 | G G K H Q L R L V P T R W A G K G L L G C N I P L Q R | 2057812 |
| 195 | V S M N - - - - - - - - - - - - - L T T P G T S S R S P | GI 2055256 |

FIGURE 7B

```
  1      MNG--KARKEAVQTAAKELLKFVNRSPSPF    2058485
  1    MAAALKPSAPEIRKAAQEFINYLNKAVTPF    GI 529706

29    HAVAECRNRLLQAGFSELKETEKWNIKPES    2058485
 31    HATQEVKDRLLQAGFTELPESGHWDIQPTS    GI 529706

59    KYFMTRNSSTIIAFAVGGQYVPGNGFSLIG    2058485
 61    KYFVTKNRSAILAFAVGGSYKPGSGFSIVV    GI 529706

89    AHTDSPCLRVKRRSRRSQVGFQQVGVETYG    2058485
 91    GHTDSPCLRVKPISHQKSDKFLQVGVSTYG    GI 529706

119    GGIWSTWFDRDLTLAGRVIVKCPTSGRLEQ    2058485
121    GGIWRTWFDRDLSVAGLVIVK--NGEKLQH    GI 529706

149    QLVHVERPILRIPHLAIHLQRNINENFGPN    2058485
149    KLIDVKKPVLFIPNLAIHLETD-RTTFKPN    GI 529706
```

FIGURE 8A

```
179 TEMHLVPILATAIQEELEKG-TPEPGPLNA    2058485
178 TETELRPILETFAAAGINAPQKPESTGFAD    GI 529706

208 ---VDERHHSVLMSLLCAHLGLSPKDIVEM    2058485
208 PRNITNNHHPQFLGLIAKEAGCQPEDIVDL    GI 529706

235 ELCLADTQPAVLGGAYDEFIFAPRLDNLHS    2058485
238 DLYLYDTNKAAIVGMEDEFISGARLDNQVG    GI 529706

265 CFCALQALIDSCAGPGSLATEPHVRMVTLY    2058485
268 TYTAISGLLESLTG-ESFKNDPQIRIAACF    GI 529706

295 DNEEVGSESAQGAQSLLTELVLRRISASCQ    2058485
297 DNEEVGSDSAMGASSFTEFVLRRLSAG-G   GI 529706

325 HPTAFEEAIPKSFMISADMAHAVHPNYLDK    2058485
326 STTAFEEAIGKSMLISADQAHATHPNYSAK    GI 529706
```

HUMAN PROTEASE ASSOCIATED PROTEINS

FIELD OF THE INVENTION

This invention relates to nucleic acid and amino acid sequences of human protease associated proteins and to the use of these sequences in the diagnosis, treatment, and prevention of cell proliferative and immune disorders.

BACKGROUND OF THE INVENTION

Proteolytic processing is an essential component of normal cell growth, differentiation, remodeling, and homeostasis. The cleavage of peptide bonds within cells is necessary for a variety of functions, including the maturation of precursor proteins to their active form, the removal of signal sequences from targeted proteins, the degradation of incorrectly folded proteins, and the controlled turnover of peptides within the cell. Proteases participate in apoptosis, inflammation, and in tissue remodeling during embryonic development, wound healing, and normal growth. They are necessary components of bacterial, parasitic, and viral invasion and replication within a host. Mammalian proteases have been identified and categorized based on active site structure, mechanism of action, and overall three-dimensional structure. (Beynon, R. J. and J. S. Bond (1994) *Proteolytic Enzymes: A Practical Approach.* Oxford University Press, New York, N.Y., pp. 1–5.)

The serine proteases (SPs) are a large family of proteolytic enzymes that include the digestive enzymes, trypsin and chymotrypsin; components of the complement and blood-clotting cascades; and enzymes that control the degradation and turnover of macromolecules of the extracellular matrix. SPs are named because of the presence of a serine residue found in the active catalytic site which forms a triad together with an aspartate and a histidine residue. SPs have a wide range of substrate specificities and can be subdivided into subfamilies on the basis of these specificities. The main sub-families are trypases, which cleave after arginine or lysine; aspases, which cleave after aspartate; chymases, which cleave after phenylalanine or leucine; metases which cleave after methionine; and serases, which cleave after serine.

Cysteine proteases are involved in diverse cellular processes ranging from the processing of precursor proteins to intracellular degradation. Mammalian cysteine proteases include lysosomal cathepsins and cytosolic calcium activated proteases, calpains. Cysteine proteases are produced by monocytes, macrophages and other cells of the immune system which migrate to sites of inflammation and secrete various molecules necessary for the repair of damaged tissue. These cells may overproduce the same molecules and cause tissue destruction in certain disorders. For example, in autoimmune diseases such as rheumatoid arthritis, the secretion of the cysteine protease, cathepsin C, degrades collagen, laminin, elastin and other structural proteins found in the extracellular matrix of bones.

Carboxypeptidases A and B are the principal mammalian representatives of the metallo-protease family. Both are exopeptidases of similar structure and active sites. Carboxypeptidase A, like chymotrypsin, prefers C-terminal aromatic and aliphatic side chains of hydrophobic nature, whereas carboxypeptidase B is directed toward basic arginine and lysine residues. Active site components include zinc, with its three ligands of two glutamic acid and one histidine residues.

Many other proteolytic enzymes do not fit any of the major categories discussed above because their mechanisms of action and/or active sites have not been elucidated. These include the aminopeptidases and signal peptidases. Aminopeptidases catalyze the hydrolysis of amino acid residues from the amino terminus of peptide substrates. Bovine leucine aminopeptidase is a zinc metallo-enzyme that utilizes the sulfhydryl groups from at least three reactive cysteine residues at its active site in the binding of metal ions. (Cuypers, H. T. et al. (1982) J. Biol. Chem. 257:7086–7091.)

Signal peptidases are a specialized class of proteases found in all prokaryotic and eukaryotic cell types that serve in the processing of signal peptides from certain proteins. Signal peptides are amino-terminal sequences on a protein which directs the protein from its ribosomal assembly site to a particular cellular or extracellular location. Once the protein has been exported, removal of the signal sequence by a signal peptidase and posttranslational processing, e.g., glycosylation or phosphorylation, activate the protein. Signal peptidases exist as multi-subunit complexes in both yeast and mammals.

Proteasome, an intracellular protease complex found in some bacteria and in all eukaryotic cells, plays an important role in cellular physiology. Proteasomes are responsible for the timely degradation of cellular proteins of all types and control proteins that function to activate or repress cellular processes such as transcription and cell cycle progression. (Ciechanover, A. (1994) Cell 79:13–21.) Proteasomes act on proteins which have been targeted for hydrolysis by the covalent attachment of a small protein called ubiquitin to lysine side chains of the protein. Ubiquitin-proteasome systems are implicated in the degradation of mitotic cyclic kinases, oncoproteins, tumor suppressor genes (p53), cell surface receptors associated with signal transduction, transcriptional regulators, and mutated or damaged proteins. (Ciechanover, supra.) Proteasomes are large (~2000 kDa), multisubunit complexes composed of a central catalytic core containing a variety of proteases and terminal subunits that serve in substrate recognition and regulation of proteasome activity.

Protease inhibitors play a major role in the regulation of the activity and effect of proteases. They have been shown to control pathogenesis in animal models of proteolytic disorders. (Murphy, G. (1991) Agents Actions Suppl 35:69–76.) In particular, low levels of the cystatins, low molecular weight inhibitors of the cysteine proteases, seem to be correlated with malignant progression of tumors. (Calkins, C. et al (1995) Biol Biochem Hoppe Seyler 376:71–80.) The balance between levels of cysteine proteases and their inhibitors is also significant in the development of disorders. Specifically, increases in cysteine protease levels, when accompanied by reductions in inhibitor activity, are correlated with increased malignant properties of tumor cells and the pathology of arthritis and immunological diseases in humans.

The Kunitz family of serine protease inhibitors are characterized by one or more "Kunitz domains" containing a series of cysteine residues that are regularly spaced over approximately 50 amino acid residues and form three intra-chain disulfide bonds. Members of this family include aprotinin, tissue factor pathway inhibitor (TFPI-1 and TFPI-2), and inter-α-trypsin inhibitor, and bikunin. (Marlor, C. W. et al. (1997) J. Biol. Chem. 272:12202–12208.) Members of this family are potent inhibitors (in the nanomolar range) against serine proteases such as kallikrein and plasmin. Aprotinin has clinical utility in reduction of perioperative blood loss.

The discovery of new human protease associated proteins and the polynucleotides encoding them satisfies a need in the art by providing new compositions which are useful in the diagnosis, treatment, and prevention of cell proliferative and immune disorders.

SUMMARY OF THE INVENTION

The invention features substantially purified polypeptides, human protease associated proteins, referred to collectively as "HPRAP" and individually as "HPRAP-1", "HPRAP-2", "HPRAP-3", and "HPRAP-4." In one aspect, the invention provides a substantially purified polypeptide comprising an amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4.

The invention further provides a substantially purified variant having at least 90% amino acid identity to the amino acid sequences of SEQ ID NO:1, SEQ ID NO:2, SEQ ID NO:3, or SEQ ID NO:4, or to a fragment of any of these sequences. The invention also provides an isolated and purified polynucleotide encoding the polypeptide comprising an amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4, as well as an isolated and purified polynucleotide having a sequence which is complementary to the polynucleotide encoding the polypeptide comprising the amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4.

The invention also provides an isolated and purified polynucleotide comprising a polynucleotide sequence selected from the group consisting of SEQ ID NO:5, SEQ ID NO:6, SEQ ID NO:7, SEQ ID NO:8, a fragment of SEQ ID NO:5, a fragment of SEQ ID NO:6, a fragment of SEQ ID NO:7, and a fragment of SEQ ID NO:8. The invention further provides an isolated and purified polynucleotide variant having at least 90% polynucleotide sequence identity to the polynucleotide sequence comprising a polynucleotide sequence selected from the group consisting of SEQ ID NO:5, SEQ ID NO:6, SEQ ID NO:7, SEQ ID NO:8, a fragment of SEQ ID NO:5, a fragment of SEQ ID NO:6, a fragment of SEQ ID NO:7, and a fragment of SEQ ID NO:8, as well as an isolated and purified polynucleotide having a sequence which is complementary to the polynucleotide comprising a polynucleotide sequence selected from the group consisting of SEQ ID NO:5, SEQ ID NO:6, SEQ ID NO:7, SEQ ID NO:8, a fragment of SEQ ID NO:5, a fragment of SEQ ID NO:6, a fragment of SEQ ID NO:7, and a fragment of SEQ ID NO:8.

The invention further provides an expression vector containing at least a fragment of the polynucleotide encoding the polypeptide comprising an amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4. In another aspect, the expression vector is contained within a host cell.

The invention also provides a method for producing a polypeptide comprising the amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4 in conjunction with a suitable pharmaceutical carrier.

The invention further includes a purified antibody which binds to a polypeptide comprising the amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4, as well as a purified agonist and a purified antagonist to the polypeptide.

The invention also provides a method for treating or preventing a cell proliferative disorder, the method comprising administering to a subject in need of such treatment an effective amount of an antagonist of the polypeptide having an amino acid sequence selected from the group consisting of SEQ ID NO:1, SEQ ID NO:3, SEQ ID NO:4, a fragment of SEQ ID NO:1, a fragment of SEQ ID NO:3, and a fragment of SEQ ID NO:4.

The invention also provides a method for treating or preventing an immune disorder, the method comprising administering to a subject in need of such treatment an effective amount of an antagonist of the polypeptide having an amino acid sequence selected from the group consisting of SEQ ID NO:1, SEQ ID NO:3, SEQ ID NO:4, a fragment of SEQ ID NO:1, a fragment of SEQ ID NO:3, and a fragment of SEQ ID NO:4.

The invention also provides a method for treating or preventing a cell proliferative disorder, the method comprising administering to a subject in need of such treatment an effective amount of a pharmaceutical composition comprising a substantially purified polypeptide having the amino acid sequence of SEQ ID NO:2, or a fragment of SEQ ID NO:2.

The invention also provides a method for treating or preventing an immune disorder, the method comprising administering to a subject in need of such treatment an effective amount of a pharmaceutical composition comprising a substantially purified polypeptide having the amino acid sequence of SEQ ID NO:2, or a fragment of SEQ ID NO:2.

The invention also provides a method for detecting a polynucleotide encoding the polypeptide comprising the amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:2, SEQ ID NO:3, SEQ ID NO:4, a fragment of SEQ ID NO:1, a fragment of SEQ ID NO:2, a fragment of SEQ ID NO:3, and a fragment of SEQ ID NO:4 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E and 1F show the amino acid sequence (SEQ ID NO:1) and nucleic acid sequence (SEQ ID NO:5) of HPRAP-1. The alignment was produced using MACDNASIS PRO software (Hitachi Software Engineering Co. Ltd., San Bruno, Calif.).

FIGS. 2A, 2B, 2C, 2D, and 2E, show the amino acid sequence (SEQ ID NO:2) and nucleic acid sequence (SEQ ID NO:6) of HPRAP-2. The alignment was produced using MACDNASIS PRO software.

FIGS. 3A, 3B, and 3C, show the amino acid sequence (SEQ ID NO:3) and nucleic acid sequence (SEQ ID NO:7) of HPRAP-3. The alignment was produced using MACDNASIS PRO software.

FIGS. 4A, 4B, 4C, 4D, and 4E, show the amino acid sequence (SEQ ID NO:4) and nucleic acid sequence (SEQ ID NO:8) of HPRAP-4. The alignment was produced using MACDNASIS PRO software.

FIGS. 5A, 5B, 5C, and 5D show the amino acid sequence alignments between HPRAP-1 (031381; SEQ ID NO:1) and an endooligopeptidase A related protein from *Oryctolagus cuniculus* (GI 2827886; SEQ ID NO:9), produced using the multisequence alignment program of LASERGENE software (DNASTAR Inc, Madison Wis.).

FIGS. 6A and 6B show the amino acid sequence alignments between HPRAP-2 (1319265; SEQ ID NO:2) and the kunitz type protease inhibitor, bikunin, from human (GI 2065529; SEQ ID NO:10), produced using the multisequence alignment program of LASERGENE software.

FIGS. 7A and 7B show the amino acid sequence alignments between HPRAP-3 (2057812; SEQ ID NO:3) and the human proteasome subunit, p27 (GI 2055256; SEQ ID NO: 11), produced using the multisequence alignment program of LASERGENE software.

FIGS. 8A, 8B, and 8C show the amino acid sequence alignments between HPRAP4 (529706; SEQ ID NO:4) and a vacuolar aminopeptidase-related protein from *Caenorhabditis elegans* (GI 529706; SEQ ID NO:12), produced using the multisequence alignment program of LASERGENE software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HPRAP," as used herein, refers to the amino acid sequences of substantially purified HPRAP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HPRAP, increases or prolongs the duration of the effect of HPRAP. Agonists may include proteins, nucleic acids, carbohydrates, or any other molecules which bind to and modulate the effect of HPRAP.

An "allelic variant," as this term is used herein, is an alternative form of the gene encoding HPRAP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HPRAP, as described herein, include those sequences with deletions, insertions, or substitutions of different nucleotides, resulting in a polynucleotide encoding HPRAP or a polypeptide with at least one functional characteristic of HPRAP. Included within this definition are polymorphisms which may or may not be readily detectable using a particular oligonucleotide probe of the polynucleotide encoding HPRAP, and improper or unexpected hybridization to allelic variants, with a locus other than the normal chromosomal locus for the polynucleotide sequence encoding HPRAP. The encoded protein may also be "altered," and may contain deletions, insertions, or substitutions of amino acid residues which produce a silent change and result in a functionally equivalent HPRAP. Deliberate amino acid substitutions may be made on the basis of similarity in polarity, charge, solubility, hydrophobicity, hydrophilicity, and/or the amphipathic nature of the residues, as long as the biological or immunological activity of HPRAP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HPRAP which are preferably about 5 to about 15 amino acids in length, most preferably 14 amino acids, and which retain some biological activity or immunological activity of HPRAP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to HPRAP, decreases the amount or the duration of the effect of the biological or immunological activity of HPRAP. Antagonists may include proteins, nucleic acids, carbohydrates, antibodies, or any other molecules which decrease the effect of HPRAP.

As used herein, the term "antibody" refers to intact molecules as well as to fragments thereof, such as Fab, F(ab')$_2$, and Fv fragments, which are capable of binding the epitopic determinant. Antibodies that bind HPRAP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HPRAP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HPRAP or fragments of HPRAP may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR Kit (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HPRAP, by Northern analysis is indicative of the presence of nucleic acids encoding HPRAP in a sample, and thereby correlates with expression of the transcript from the polynucleotide encoding HPRAP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HPRAP. For example, modulation may cause an increase or a decrease in protein activity, binding characteristics, or any other biological, functional, or immunological properties of HPRAP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HPRAP, or fragments thereof, or HPRAP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature.

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50 % formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HPRAP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

THE INVENTION

The invention is based on the discovery of new human protease associated proteins (HPRAP), the polynucleotides encoding HPRAP, and the use of these compositions for the diagnosis, treatment, or prevention of cell proliferative and immune disorders.

Nucleic acids encoding the HPRAP-1 of the present invention were first identified in Incyte Clone 031381 from the promonocyte cell line cDNA library (THP1NOB01) using a computer search, e.g., BLAST, for amino acid sequence alignments. A consensus sequence, SEQ ID NO:5, was derived from the following overlapping and/or extended nucleic acid sequences: Incyte Clones 031381 (THP1NOB01), 3618224 (EPIPNOT01), 991115

(COLNNOT11), 1223519 (COLNTUT02), 1723492 (BLADNOT06), 599353 (BRSTNOT02), 2132359 (OVARNOT03), 853456 (NGANNOT01), and 673630 (CRBLNOT01).

In one embodiment, the invention encompasses a polypeptide comprising the amino acid sequence of SEQ ID NO:1, as shown in FIGS. 1A, 1B, 1C, 1D, 1E, and 1F. HPRAP-1 is 460 amino acids in length and has a potential N-glycosylation site at residue N299, and potential phosphorylation sites for cAMP- and cGMP-dependent protein kinase at T132, for casein kinase II at S11, S29, S95, S135, S155, and S310, for protein kinase C at S11, S23, S90, T191, S231, S247, S282, S331, S344, and S404, and for tyrosine kinase at Y87. As shown in FIGS. 5A, 5B, 5C, and 5D, HPRAP-1 has chemical and structural similarity with an endooligopeptidase A related protein from O. cuniculus (GI 2827886; SEQ ID NO:9). In particular, HPRAP-1 and the endooligopeptidase A related protein share 89% identity, including the potential N-glycosylation site and most of the potential phosphorylation sites found in HPRAP-1. The fragment of SEQ ID NO:5 from about nucleotide 1152 to about nucleotide 1205 is useful, for example, as a hybridization probe. Northern analysis shows the expression of this sequence in various libraries, at least 48% of which are immortalized or cancerous and at least 36% of which involve immune response. Of particular note is the expression of HPRAP-1 in cardiovascular and gastrointestinal tissues.

Nucleic acids encoding the HPRAP-2 of the present invention were first identified in Incyte Clone 1319265 from the bladder tissue cDNA library (BLADNOT04) using a computer search, e.g., BLAST, for amino acid sequence alignments. A consensus sequence, SEQ ID NO:6, was derived from the following overlapping and/or extended nucleic acid sequences: Incyte Clones 1319265 (BLADNOT04), 1522685 (BLADTUT04), 872599 and 875890 (LUNGAST01), 1427703 (SINTBST01), 1224264 (COLNTUT02), and 1493438 (PROSNON01).

In another embodiment, the invention encompasses a polypeptide comprising the amino acid sequence of SEQ ID NO:2, as shown in FIGS. 2A, 2B, 2C, 2D, 2E. HPRAP-2 is 349 amino acids in length and has two potential N-glycosylation sites at residues N53 and N342, and potential phosphorylation sites for casein kinase II at T43, S169, S193, S264, S331, and T332, and for protein kinase C at S60, S71, S205, S259, S264, and T344. HPRAP-2 contains a potential signal peptide sequence between residues M1 and P48 and a potential transmembrane domain between residues M285 and C305. HPRAP-2 also contains two sequences related to the Kunitz family domains between residues C94 and C119, and residues C235 and C260. As shown in FIGS. 6A and 6B, HPRAP-2 has chemical and structural similarity with the kunitz type protease inhibitor, bikunin, from human (GI 2065529; SEQ ID NO:10). In particular, HPRAP-2 and human bikunin share 25% identity, including 12 cysteine residues located in the two kunitz domains in both proteins. The fragment of SEQ ID NO:6 from about nucleotide 500 to about nucleotide 563 is useful, for example, as a hybridization probe. Northern analysis shows the expression of this sequence in various libraries, at least 60% of which are immortalized or cancerous and at least 41% of which involve immune response. Of particular note is the expression of HPRAP-2 in reproductive and gastrointestinal tissues.

Nucleic acids encoding the HPRAP-3 of the present invention were first identified in Incyte Clone 2057812 from the bronchial epithelium cDNA library (BEPINOT01) using a computer search, e.g., BLAST, for amino acid sequence alignments. A consensus sequence, SEQ ID NO:7, was derived from the following overlapping and/or extended nucleic acid sequences: Incyte Clones 2057812 (BEPINOT01), 2496092 (ADRETUT05), and 026889 (SPLNFET01).

In another embodiment, the invention encompasses a polypeptide comprising the amino acid sequence of SEQ ID NO:3, as shown in FIGS. 3A, 3B, and 3C. HPRAP-3 is 239 amino acids in length and has a potential N-glycosylation site at residue N204, and potential phosphorylation sites for casein kinase II at S2, T19, and S65, and for protein kinase C at S46, T74, and S121. As shown in FIGS. 7A and 7B, HPRAP-3 has chemical and structural similarity with the human proteasome subunit, p27 (GI 2055256; SEQ ID NO:11). In particular, HPRAP-3 and p27 share 87% identity. The fragment of SEQ ID NO:7 from about nucleotide 551 to about nucleotide 604 is useful, for example, as a hybridization probe. Northern analysis shows the expression of this sequence in various libraries, at least 51 % of which are immortalized or cancerous and at least 36% of which involve immune response. Of particular note is the expression of HPRAP-3 in cardiovascular, hematopoietic/immune, nervous, and reproductive tissues.

Nucleic acids encoding the HPRAP-4 of the present invention were first identified in Incyte Clone 2058485 from the ovarian tissue cDNA library (OVARNOT03) using a computer search, e.g., BLAST, for amino acid sequence alignments. A consensus sequence, SEQ ID NO:8, was derived from the following overlapping and/or extended nucleic acid sequences: Incyte Clones 2058485 (OVARNOT03), 3115916 (LUNGTUT13), 556715 (MPHGLPT02), 2023129 (CONNNOT01), 1513114 (PANCTUT01), 2023129 (CONNNOT01), and 1964262 (BRSTNOT04).

In another embodiment, the invention encompasses a polypeptide comprising the amino acid sequence of SEQ ID NO:4, as shown in FIGS. 4A, 4B, 4C, 4D, and 4E. HPRAP-4 is 471 amino acids in length and has a potential N-glycosylation site at residue N65, and potential phosphorylation sites for cAMP- and cGMP-dependent protein kinase at S102 and S320, for casein kinase II at T124, S227, T292, T327, and S437, and for protein kinase C at T49, S102, S143, S227, and S437. As shown in FIGS. 8A, 8B, and 8C, HPRAP-4 shares chemical and structural similarity with a vacuolar aminopeptidase-related protein from C. elegans (GI 529706; SEQ ID NO:12). In particular, HPRAP-4 and the vacuolar aminopeptidase-related protein share 46% identity. Fragments of SEQ ID NO:8 from about nucleotide 254 to about nucleotide 319, and from about nucleotide 1025 to about nucleotide 1097 are useful, for example, as hybridization probes. Northern analysis shows the expression of this sequence in various libraries, at least 50% of which are immortalized or cancerous and at least 32% of which involve immune response. Of particular note is the expression of HPRAP-4 in reproductive and gastrointestinal tissues.

The invention also encompasses HPRAP variants. A preferred HPRAP variant is one which has at least about 80%, more preferably at least about 90%, and most preferably at least about 95% amino acid sequence identity to the HPRAP amino acid sequence, and which contains at least one functional or structural characteristic of HPRAP.

The invention also encompasses polynucleotides which encode HPRAP. In a particular embodiment, the invention encompasses a polynucleotide sequence selected from the group consisting of SEQ ID NO:5, SEQ ID NO:6, SEQ ID NO:7, and SEQ ID NO:8, which encodes an HPRAP.

The invention also encompasses a variant of a polynucleotide sequence encoding HPRAP. In particular, such a variant polynucleotide sequence will have at least about 80%, more preferably at least about 90%, and most preferably at least about 95% polynucleotide sequence identity to the polynucleotide sequence encoding HPRAP. A particular aspect of the invention encompasses a variant of SEQ ID NO:2 which has at least about 80%, more preferably at least about 90%, and most preferably at least about 95% polynucleotide sequence identity to a polynucleotide sequence selected from the group consisting of SEQ ID NO:5, SEQ ID NO:6, SEQ ID NO:7, and SEQ ID NO:8. Any one of the polynucleotide variants described above can encode an amino acid sequence which contains at least one functional or structural characteristic of HPRAP.

It will be appreciated by those skilled in the art that as a result of the degeneracy of the genetic code, a multitude of polynucleotide sequences encoding HPRAP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HPRAP, and all such variations are to be considered as being specifically disclosed.

Although nucleotide sequences which encode HPRAP and its variants are preferably capable of hybridizing to the nucleotide sequence of the naturally occurring HPRAP under appropriately selected conditions of stringency, it may be advantageous to produce nucleotide sequences encoding HPRAP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HPRAP and its derivatives without altering the encoded amino acid sequences include the production of RNA transcripts having more desirable properties, such as a greater half-life, than transcripts produced from the naturally occurring sequence.

The invention also encompasses production of DNA sequences which encode HPRAP and HPRAP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HPRAP or any fragment thereof.

Also encompassed by the invention are polynucleotide sequences that are capable of hybridizing to the claimed polynucleotide sequences, and, in particular, to those shown in SEQ ID NO:5, SEQ ID NO:6, SEQ ID NO:7, SEQ ID NO:8, a fragment of SEQ ID NO:5, a fragment of SEQ ID NO:6, a fragment of SEQ ID NO:7, and a fragment of SEQ ID NO:8 under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASET amplification system (GIBCO BRL, Gaithersburg, Md.). Preferably, the process is automated with machines such as the MICROLAB 2200 system (Hamilton, Reno, Nev.), DNA ENGINE thermal cycler (PTC200; MJ Research, Watertown, Mass.) and the ABI Catalyst and ABI PRISM 373 and 377 sequencing systems (Perkin Elmer).

The nucleic acid sequences encoding HPRAP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto, Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HPRAP may be cloned in recombinant DNA molecules that direct expression of HPRAP, or fragments or functional equivalents thereof, in appropriate host cells. Due to the inherent degeneracy of the genetic code, other DNA sequences which encode substantially the same or a functionally equivalent amino acid sequence may be produced and used to express HPRAP.

The nucleotide sequences of the present invention can be engineered using methods generally known in the art in order to alter HPRAP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HPRAP may be synthesized, in whole or in part, using chemical methods well known in the art. (See, e.g., Caruthers, M. H. et al. (1980) Nucl. Acids Symp. Ser. (7):215–223, and Horn, T. et al. (1980) Nucl. Acids Symp. Ser. (7):225–232.) Alternatively, HPRAP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin Elmer). Additionally, the amino acid sequence of HPRAP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active HPRAP, the nucleotide sequences encoding HPRAP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HPRAP. Such elements may vary in their strength and specificity. Specific initiation signals may also be used to achieve more efficient translation of sequences encoding HPRAP. Such signals include the ATG initiation codon and adjacent sequences, e.g. the Kozak sequence. In cases where sequences encoding HPRAP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HPRAP and appropriate transcriptional and translational control elements. These methods include in vitro recombinant DNA techniques, synthetic techniques, and in vivo genetic recombination. (See, e.g., Sambrook, J. et al. (1989) *Molecular Cloning. A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HPRAP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HPRAP. For example, routine cloning, subcloning, and propagation of polynucleotide sequences encoding HPRAP can be achieved using a multifunctional *E. coli* vector such as PBLUESCRIPT (Stratagene) or PSPORT1 plasmid (Life Technologies, Gaithersburg Md.). Ligation of sequences encoding HPRAP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of HPRAP are needed, e.g. for the production of antibodies, vectors which direct high level expression of HPRAP may be used. For example, vectors containing the strong, inducible T5 or T7 bacteriophage promoter may be used.

Yeast expression systems may be used for production of HPRAP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of HPRAP. Transcription of sequences encoding HPRAP may be driven by viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding HPRAP may be ligated into an adenovirus transcription/translation complex consisting of the late promoter and tripartite leader sequence. Insertion in a non-essential E1 or E3 region of the viral genome may be used to obtain infective virus which expresses HPRAP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of HPRAP in cell lines is preferred. For example, sequences encoding HPRAP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ or apr$^-$ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Nati. Acad. Sci. 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HPRAP is inserted within a marker gene sequence, transformed cells containing sequences encoding HPRAP can be identified by the absence of marker gene function. Alternatively, a marker gene can be placed in tandem with a sequence encoding HPRAP under the control of a single promoter. Expression of the marker gene in response to induction or selection usually indicates expression of the tandem gene as well.

In general, host cells that contain the nucleic acid sequence encoding HPRAP and that express HPRAP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HPRAP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HPRAP is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HPRAP include oligolabeling, nick translation, end-labeling, or PCR amplification using a labeled nucleotide. Alternatively, the sequences encoding HPRAP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech (Piscataway, N.J.), Promega (Madison, Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HPRAP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HPRAP may be designed to contain signal sequences which direct secretion of HPRAP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding HPRAP may be ligated to a heterologous sequence resulting in translation of a fusion protein in any of the aforementioned host systems. For example, a chimeric HPRAP protein containing a heterologous moiety that can be recognized by a commercially available antibody may facilitate the screening of peptide libraries for inhibitors of HPRAP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HPRAP encoding sequence and the heterologous protein sequence, so that HPRAP may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled HPRAP may be achieved in vitro using the TNT rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HPRAP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the ABI 431A peptide synthesizer (Perkin Elmer). Various fragments of HPRAP may be synthesized separately and then combined to produce the full length molecule.

THERAPEUTICS

Chemical and structural similarity exists between HPRAP-1 and an endooligopeptidase A related protein from *O. cuniculus* (GI 2827886). In addition, HPRAP-1 is expressed in cancer and immortalized cell lines and tissues associated with inflammation and the immune response. Therefore, HPRAP-1 appears to play a role in cell proliferative and immune disorders.

Chemical and structural similarity exists between HPRAP-2 and the kunitz type protease inhibitor, bikunin, from human (GI 2065529). In addition, HPRAP-2 is expressed in cancer and immortalized cell lines and tissues associated with inflammation and the immune response. Therefore, HPRAP-2 appears to play a role in cell proliferative and immune disorders.

Chemical and structural similarity exists between HPRAP-3 and the human proteasome subunit, p27 (GI 2055256). In addition, HPRAP-3 is expressed in cancer and immortalized cell lines and tissues associated with inflammation and the immune response. Therefore, HPRAP-3 appears to play a role in cell proliferative and immune disorders.

Chemical and structural similarity exists between HPRAP-4 and a vacuolar aminopeptidase-related protein from *C. elegans* (GI 529706). In addition, HPRAP-4 is expressed in cancer and immortalized cell lines and tissues associated with inflammation and the immune response. Therefore, HPRAP-4 appears to play a role in cell proliferative and immune disorders.

Therefore, in one embodiment, HPRAP-2 or a fragment or derivative thereof may be administered to a subject to treat or prevent a cell proliferative disorder. Such disorders can include, but are not limited to, actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HPRAP-2 or a fragment or derivative thereof may be administered to a subject to treat or prevent a cell proliferative disorder including, but not limited to, those described above.

In a further embodiment, a pharmaceutical composition comprising a substantially purified HPRAP-2 in conjunction with a suitable pharmaceutical carrier may be administered to a subject to treat or prevent a cell proliferative disorder including, but not limited to, those provided above.

In still another embodiment, an agonist which modulates the activity of HPRAP-2 may be administered to a subject to treat or prevent a cell proliferative disorder including, but not limited to, those listed above.

In another embodiment, HPRAP-2 or a fragment or derivative thereof may be administered to a subject to treat or prevent an immune disorder. Such disorders can include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing HPRAP-2 or a fragment or derivative thereof may be administered to a subject to treat or prevent an immune disorder including, but not limited to, those described above.

In a further embodiment, a pharmaceutical composition comprising a substantially purified HPRAP-2 in conjunction with a suitable pharmaceutical carrier may be administered to a subject to treat or prevent an immune disorder including, but not limited to, those provided above.

In still another embodiment, an agonist which modulates the activity of HPRAP-2 may be administered to a subject to treat or prevent an immune disorder including, but not limited to, those listed above.

In a further embodiment, an antagonist of HPRAP-1 may be administered to a subject to treat or prevent a cell proliferative disorder. Such a disorder may include, but is not limited to, those discussed above. In one aspect, an antibody which specifically binds HPRAP-1 may be used directly as an antagonist or indirectly as a targeting or delivery mechanism for bringing a pharmaceutical agent to cells or tissue which express HPRAP-1.

In an additional embodiment, a vector expressing the complement of the polynucleotide encoding HPRAP-1 may be administered to a subject to treat or prevent a cell proliferative disorder including, but not limited to, those described above.

In a further embodiment, an antagonist of HPRAP-3 may be administered to a subject to treat or prevent a cell proliferative disorder. Such a disorder may include, but is not limited to, those discussed above. In one aspect, an antibody which specifically binds HPRAP-3 may be used directly as an antagonist or indirectly as a targeting or delivery mechanism for bringing a pharmaceutical agent to cells or tissue which express HPRAP-3.

In an additional embodiment, a vector expressing the complement of the polynucleotide encoding HPRAP-3 may be administered to a subject to treat or prevent a cell proliferative disorder including, but not limited to, those described above.

In a further embodiment, an antagonist of HPRAP-4 may be administered to a subject to treat or prevent a cell proliferative disorder. Such a disorder may include, but is not limited to, those discussed above. In one aspect, an antibody which specifically binds HPRAP-4 may be used directly as an antagonist or indirectly as a targeting or delivery mechanism for bringing a pharmaceutical agent to cells or tissue which express HPRAP-4.

In an additional embodiment, a vector expressing the complement of the polynucleotide encoding HPRAP-4 may be administered to a subject to treat or prevent a cell proliferative disorder including, but not limited to, those described above.

In a further embodiment, an antagonist of HPRAP-1 may be administered to a subject to treat or prevent an immune disorder. Such a disorder may include, but is not limited to, those discussed above. In one aspect, an antibody which specifically binds HPRAP-1 may be used directly as an antagonist or indirectly as a targeting or delivery mechanism for bringing a pharmaceutical agent to cells or tissue which express HPRAP-1.

In an additional embodiment, a vector expressing the complement of the polynucleotide encoding HPRAP-1 may be administered to a subject to treat or prevent an immune disorder including, but not limited to, those described above.

In a further embodiment, an antagonist of HPRAP-3 may be administered to a subject to treat or prevent an immune disorder. Such a disorder may include, but is not limited to, those discussed above. In one aspect, an antibody which specifically binds HPRAP-3 may be used directly as an antagonist or indirectly as a targeting or delivery mechanism for bringing a pharmaceutical agent to cells or tissue which express HPRAP-3.

In an additional embodiment, a vector expressing the complement of the polynucleotide encoding HPRAP-3 may be administered to a subject to treat or prevent an immune disorder including, but not limited to, those described above.

In a further embodiment, an antagonist of HPRAP-4 may be administered to a subject to treat or prevent an immune disorder. Such a disorder may include, but is not limited to, those discussed above. In one aspect, an antibody which specifically binds HPRAP-4 may be used directly as an antagonist or indirectly as a targeting or delivery mechanism for bringing a pharmaceutical agent to cells or tissue which express HPRAP-4.

In an additional embodiment, a vector expressing the complement of the polynucleotide encoding HPRAP-4 may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HPRAP may be produced using methods which are generally known in the art. In particular, purified HPRAP may be used to produce antibodies or to screen libraries of pharmaceutical agents to identify those which specifically bind HPRAP. Antibodies to HPRAP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HPRAP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HPRAP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HPRAP amino acids may be fused with those of another protein, such as KLH, and antibodies to the chimeric molecule may be produced.

Monoclonal antibodies to HPRAP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HPRAP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HPRAP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPRAP and its specific antibody. A two-site, monoclonal-based immunoassay utilizing monoclonal antibodies reactive to two non-interfering HPRAP epitopes is preferred, but a competitive binding assay may also be employed. (Maddox, supra.)

In another embodiment of the invention, the polynucleotides encoding HPRAP, or any fragment or complement thereof, may be used for therapeutic purposes. In one aspect, the complement of the polynucleotide encoding HPRAP may be used in situations in which it would be desirable to block the transcription of the mRNA. In particular, cells may be transformed with sequences complementary to polynucleotides encoding HPRAP. Thus, complementary molecules or fragments may be used to modulate HPRAP activity, or to achieve regulation of gene function. Such technology is now well known in the art, and sense or antisense oligonucleotides or larger fragments can be designed from various locations along the coding or control regions of sequences encoding HPRAP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HPRAP. (See, e.g., Sambrook, supra; and Ausubel, supra.)

Genes encoding HPRAP can be turned off by transforming a cell or tissue with expression vectors which express high levels of a polynucleotide, or fragment thereof, encoding HPRAP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HPRAP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HPRAP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HPRAP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'-O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HPRAP, antibodies to HPRAP, and mimetics, agonists, antagonists, or inhibitors of HPRAP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HPRAP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HPRAP or fragments thereof, antibodies of HPRAP, and agonists, antagonists or inhibitors of HPRAP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HPRAP may be used for the diagnosis of disorders characterized by expression of HPRAP, or in assays to monitor patients being treated with HPRAP or agonists, antagonists, or inhibitors of HPRAP. Antibodies useful for diagnostic purposes may be prepared in the same manner as described above for therapeutics. Diagnostic assays for HPRAP include methods which utilize the antibody and a label to detect HPRAP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HPRAP, including ELISAs, RIAs, and FACS, are known in the art and provide a basis for diagnosing altered or abnormal levels of HPRAP expression. Normal or standard values for HPRAP expression are established by combining body fluids or cell extracts taken from normal mammalian subjects, preferably human, with antibody to HPRAP under conditions suitable for complex formation The amount of standard complex formation may be quantitated by various methods, preferably by photometric means. Quantities of HPRAP expressed in subject, control, and disease samples from biopsied tissues are compared with the standard values. Deviation between standard and subject values establishes the parameters for diagnosing disease.

In another embodiment of the invention, the polynucleotides encoding HPRAP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HPRAP may be correlated with disease. The diagnostic assay may be used to determine absence, presence, and excess expression of HPRAP, and to monitor regulation of HPRAP levels during therapeutic intervention.

In one aspect, hybridization with PCR probes which are capable of detecting polynucleotide sequences, including genomic sequences, encoding HPRAP or closely related molecules may be used to identify nucleic acid sequences which encode HPRAP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HPRAP, allelic variants, or related sequences.

Probes may also be used for the detection of related sequences, and should preferably have at least 50% sequence identity to any of the HPRAP encoding sequences. The hybridization probes of the subject invention may be DNA or RNA and may be derived from the sequences of SEQ ID NO:5, SEQ ID NO:6, SEQ ID NO:7, or SEQ ID NO:8 or from genomic sequences including promoters, enhancers, and introns of the HPRAP gene.

Means for producing specific hybridization probes for DNAs encoding HPRAP include the cloning of polynucleotide sequences encoding HPRAP or HPRAP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}p$ or 35S, or by enzymatic labels, such as alkaline phosphatase coupled to the probe via avidin/biotin coupling systems, and the like.

Polynucleotide sequences encoding HPRAP may be used for the diagnosis of a disorder associated with expression of HPRAP. Examples of such a disorder include, but are not limited to, cell proliferative disorders such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding HPRAP may be used in Southern or Northern analysis, dot blot, or other membrane-based technologies; in PCR technologies; in dipstick, pin, and ELISA assays; and in microarrays utilizing fluids or tissues from patients to detect altered HPRAP expression. Such qualitative or quantitative methods are well known in the art.

In a particular aspect, the nucleotide sequences encoding HPRAP may be useful in assays that detect the presence of associated disorders, particularly those mentioned above. The nucleotide sequences encoding HPRAP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HPRAP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HPRAP, a normal or standard profile for expression is established. This may be accomplished by combining body fluids or cell extracts taken from normal subjects, either animal or human, with a sequence, or a fragment thereof, encoding HPRAP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HPRAP may involve the use of PCR. These oligomers may be chemically synthesized, generated enzymatically, or produced in vitro. Oligomers will preferably contain a fragment of a polynucleotide encoding HPRAP, or a fragment of a polynucleotide complementary to the polynucleotide encoding HPRAP, and will be employed under optimized conditions for identification of a specific gene or condition. Oligomers may also be employed under less stringent conditions for detection or quantitation of closely related DNA or RNA sequences.

Methods which may also be used to quantitate the expression of HPRAP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HPRAP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HPRAP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HPRAP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HPRAP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HPRAP, or fragments thereof, and washed. Bound HPRAP is then detected by methods well known in the art. Purified HPRAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPRAP specifically compete with a test compound for binding HPRAP. In this manner, antibodies can be used to detect the presence of any peptide which shares one or more antigenic determinants with HPRAP.

In additional embodiments, the nucleotide sequences which encode HPRAP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

THP1NOB01

The THP1NOB01 Library was constructed using RNA isolated from cultured, unstimulated THP-1 cells. THP-1 (ATCC TIB 202) is a human promonocyte line derived from the peripheral blood of a 1-year-old Caucasian male with acute monocytic leukemia. The THP1NOB01 cDNA library was custom constructed in the Uni-ZAP vector system by Stratagene (La Jolla, Calif.).

BLADNOT04

The BLADNOT04 Library was constructed using 1 microgram of polyA RNA isolated from bladder tissue of a 28-year-old Caucasian male who died from a self-inflicted gunshot wound (specimen #RA95-09-0677; International Institute of Advanced Medicine, Exton, Pa.). The tissue donor had a history of smoking and substance abuse.

BEPINOT01

The BEPINOT01 1 Library was constructed using 1.1 micrograms of polyA RNA isolated from a bronchial epithelium (NHBE) primary cell line derived from a 54-year-old Caucasian male.

OVARNOT03

The OVARNOT03 Library was constructed using 1 microgram of polyA RNA isolated from nontumorous ovarian tissue removed from a 43-year-old Caucasian female during a bilateral salpingo-oopherectomy (removal of the fallopian tubes and ovaries). Family history included atherosclerotic coronary artery disease, cerebrovascular disease, and breast, pancreatic and uterine cancer.

BLADNOT04, BEPINOT01, and OVARNOT03

The frozen tissue was homogenized and lysed using a POLYTRON homogenizer PT-3000 (Brinkmann Instruments, Westbury, N.J.) in guanidinium isothiocyanate solution. The lysate was centrifuged over a 5.7 M CsCl cushion using an Beckman SW28 rotor in a L8-70M ultracentrifuge (Beckman Coulter Fullerton, Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated with the OLIGOTEX kit (QIAGEN, Inc., Chatsworth, Calif.) and used to construct the cDNA library.

The mRNAs were handled according to the recommended protocols in the SUPERSCRIPT plasmid system (Cat. #18248-013; Life Technologies, Gaithersburg, Md.). cDNAs were fractionated on a SEPHAROSE column CL4B (Cat. #275105-01; Amersham Pharmacia Upjohn), and those cDNAs exceeding 400 bp were ligated into either the PSPORT1 (Life Technologies) or PINCY vector (Incyte Pharmaceuticals). The plasmid was subsequently transformed into DH5α or DH12S competent cells (Life Technologies).

II. Isolation and Sequencing of cDNA Clones

For BLADNOT04 and BEPINOT01, plasmid DNA was released from the cells and purified using the REAL Prep 96 plasmid kit (Catalog #26173; QIAGEN, Inc.). For OVARNOT03, plasmid or phagemid DNA was released from cells and purified using the MINIPREP Kit (Cat. No. 77468; Advanced Genetic Technologies Corporation, Gaithersburg Md.). The recommended protocol was employed except for the following changes: 1) the bacteria were cultured in 1 ml of sterile Terrific Broth (Catalog #22711, Gibco BRL Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2200 system (Hamilton, Reno, Nev.) in combination with DNA ENGINE thermal cycler (PTC200 from MJ Research, Watertown, Mass.) and ABI PRISMS DNA sequencing systems (Perkin Elmer).

III. Similarity Searching of cDNA Clones and Their Deduced Proteins
BLADNOT04, BEPINOT01, and OVARNOT03

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.
THP1NOB01

Each cDNA was compared to sequences in GenBank using a search algorithm developed by Applied Biosystems and incorporated into the INHERIT 670 sequence analysis system (Applied Biosystems). In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. and Henikoff G. P. (1991) Nucleic Acids Res. 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probalistic approach which analyzes consensus primary structures of gene families. (See, e.g., Eddy, S. R. (1996) Cur. Opin. Str. Biol. 6:361–365.)

The PFAM database contains protein sequences of 527 protein families gathered from publicly available sources, e.g., SWISS-PROT and PROSITE. PFAM searches for well characterized protein domain families using two highquality alignment routines, seed alignment and full alignment. (See, e.g., Sonnhammer, E. L. L. et al. (1997) Proteins 28:405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1% false-positives, yielding a correlation coefficient of about 0.87–0.90 for SIGPEPT. A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding HPRAP occurs. Abundance and percent abundance are also reported. Abundance directly reflects the number of times a particular transcript is represented in a cDNA library, and percent abundance is abundance divided by the total number of sequences examined in the cDNA library.

V. Extension of HPRAP Encoding Polynucleotides

The nucleic acid sequences of Incyte Clones 031381, 1319265, 2057812, and 2058485 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the DNA ENGINE thermal cycler (PTC200; M.J. Research, Watertown, Mass.), beginning with 40 pmol of each primer and the recommended concentrations of all other components of the kit, with the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent *E. coli* cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2× carb). The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:5, SEQ ID NO:6, SEQ ID NO:7, and SEQ ID NO:8 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:5, SEQ ID NO:6, SEQ ID NO:7, and SEQ ID NO:8 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [$\gamma$-$^{32}$P] adenosine triphosphate (Amersham, Chicago, Ill.), and T4 polynucleotide kinase (DuPont NEN, Boston, Mass.). The labeled oligonucleotides are substantially purified using a SEPHADEX G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7% agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak) is exposed to the blots for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HPRAP-encoding sequences, or any parts thereof, are used to detect, decrease, or inhibit expression of naturally occurring HPRAP. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of HPRAP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HPRAP-encoding transcript.

IX. Expression of HPRAP

Expression and purification of HPRAP is achieved using bacterial or virus-based expression systems. For expression of HPRAP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HPRAP upon induction with isopropyl beta-D-thiogalactopyranoside (IPTG). Expression of HPRAP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HPRAP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, HPRAP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from HPRAP at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified HPRAP obtained by these methods can be used directly in the following activity assay.

X. Demonstration of HPRAP Activity

The protease activity of HPRAP-1 and HPRAP-4 is measured by the hydrolysis of appropriate synthetic peptide substrates conjugated with various chromogenic molecules in which the degree of hydrolysis is quantitated by spectrophotometric (or fluorometric) absorption of the released chromophore. (Beynon, R. J. and J. S. Bond (1994) *Proteolytic Enzymes: A Practical Approach*. Oxford University Press, New York, N.Y., pp.25–55.) Peptide substrates are designed according to the category of protease activity as endopeptidase (serine, cysteine, aspartic proteases), aminopeptidase (leucine aminopeptidase), or carboxypeptidase (Carboxypeptidase A and B, procollagen C-proteinase). Chromogens commonly used are 2-naphthylamine, 4-nitroaniline, and furylacrylic acid. Assays are performed at-ambient temperature and contain an aliquot of the enzyme and the appropriate substrate in a suitable buffer. Reactions are carried out in an optical cuvette and followed by the increase/decrease in absorbance of the chromogen released during hydrolysis of the peptide substrate. The change in absorbance is proportional to the enzyme activity in the assay.

The assay for HPRAP-3 is carried out as described above using as the source of protease activity, a proteasome complex reconstituted with HPRAP-3 in the absence of the p27 subunit.

The assay for HPRAP-2 is carried out as described above for HPRAP-1 and HPRAP-4 using a serine protease assayed in the absence and in the presence of various concentrations of HPRAP-2. Inhibition of serine protease activity is proportional to the activity of HPRAP-2 in the assay.

XI. Functional Assays

HPRAP function is assessed by expressing the sequences encoding HPRAP at physiologically elevated levels in mammalian cell culture systems. cDNA is subcloned into a mammalian expression vector containing a strong promoter that drives high levels of cDNA expression. Vectors of choice include PCMV SPORT vector (Life Technologies, Gaithersburg, Md.) and PCR 3.1 vector (Invitrogen, Carlsbad, Calif.), both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of HPRAP on gene expression can be assessed using highly purified populations of cells transfected with sequences encoding HPRAP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding HPRAP and other genes of interest can be analyzed by Northern analysis or microarray techniques.

XII. Production of HPRAP Specific Antibodies

HPRAP substantially purified using polyacrylamide gel electrophoresis (PAGE)(see, e.g., Harrington, M. G. (1990) Methods Enzymol. 182:488–495), or other purification techniques, is used to immunize rabbits and to produce antibodies using standard protocols.

Alternatively, the HPRAP amino acid sequence is analyzed using LASERGENE software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an ABI 431A peptide synthesizer (Perkin Elmer) using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HPRAP Using Specific Antibodies

Naturally occurring or recombinant HPRAP is substantially purified by immunoaffinity chromatography using antibodies specific for HPRAP. An immunoaffinity column is constructed by covalently coupling anti-HPRAP antibody to an activated chromatographic resin, such as CNBr-activated SEPHAROSE (Pharmacia & Upjohn). After the coupling, the resin is blocked and washed according to the manufacturer's instructions.

Media containing HPRAP are passed over the immunoaffinity column, and the column is washed under conditions that allow the preferential absorbance of HPRAP (e.g., high ionic strength buffers in the presence of detergent). The column is eluted under conditions that disrupt antibody/HPRAP binding (e.g., a buffer of pH 2 to pH 3, or a high concentration of a chaotrope, such as urea or thiocyanate ion), and HPRAP is collected.

XIV. Identification of Molecules Which Interact with HPRAP

HPRAP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HPRAP, washed, and any wells with labeled HPRAP complex are assayed. Data obtained using different concentrations of HPRAP are used to calculate values for the number, affinity, and association of HPRAP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising an amino acid sequence of SEQ ID NO:1.

2. An isolated and purified polynucleotide variant having at least 90% polynucleotide sequence identity to the polynucleotide of claim 1, wherein said variant encodes a polypeptide having protease activity.

3. A probe comprising the polynucleotide of claim 1.

4. An isolated and purified polynucltide having a sequence which is completely complementary to the polynucleotide sequence of claim 1.

5. An isolated and purified polynucleotide comprising a polynucleotide sequence of SEQ ID NO:5.

6. An isolated and purified polynucleotide variant having at least 90% polynucleotide sequence identity to the polynucleotide of claim 5, wherein said variant encodes a polypeptide having protease activity.

7. An isolated and purified polynucleotide having a sequence which is completely complementary to the polynucleotide of claim 5.

8. An expression vector comprising the polynucleotide of claim 1.

9. A host cell comprising the expression vector of claim 8.

10. A method for producing a polypeptide, the method comprising the steps of:
    a) culturing the host cell of claim 9 under conditions suitable for the expression of the polypeptide; and
    b) recovering the polypeptide from the host cell culture.

11. A method for detecting a polynucleotide in a sample, the method comprising the steps of:
    (a) hybridizing the polynucleotide of claim 4 to at least one of the nucleic acids in the sample, thereby forming a hybridization complex; and
    (b) detecting the hybridization complex, wherein the presence of the hybridization complex correlates with the presence of the polynucleotide encoding the polypeptide in the sample.

12. The method of claim 11 wherein the nucleic acids of the biological sample are amplified by the polymerase chain reaction prior to the hybridizing step.

13. A method of using a polynucleotide to screen a library of molecules or compounds to identify at least one molecule or compound which specifically binds the polynucleotide, the method comprising:
    a) combining the polynucleotide of claim 1 with a library of molecules or compounds under conditions to allow specific binding, and
    b) detecting specific binding, thereby identifying a molecule or compound which specifically binds the polynucleotide.

14. The method of claim 13 wherein the library is selected from DNA molecules, RNA molecules, artificial chromosome constructions, peptides, and proteins.

15. A method of using a polynucleotide to purify a molecule or compound which specifically binds the polynucleotide from a sample, the method comprising:

a) combining the polynucleotide of claim 1 with a sample under conditions to allow specific binding, and b) detecting specific binding between the polynucleotide and a molecule or compound, c) recovering the bound polynucleotide, and d) separating the polynucleotide from the molecule or compound, thereby obtaining a purified molecule or compound.

* * * * *

SEQUENCE LISTING (1) GENERAL INFORMATION:

(iii) NUMBER OF SEQUENCES: 12

(2) INFORMATION FOR SEQ ID NO:    1:

(i) SEQUENCE CHARACTERISTICS:
      (A) LENGTH: 459 amino acids
      (B) TYPE: amino acid
      (C) STRANDEDNESS: single
      (D) TOPOLOGY: linear (vii) IMMEDIATE SOURCE:
      (A) LIBRARY: THP1NOB01
      (B) CLONE: 031381

(xi) SEQUENCE DESCRIPTION: SEQ ID NO: 1 :

```
Met Asp Gly Glu Asp Ile Pro Asp Phe Ser Ser Leu Lys Glu Glu
                 5                  10                  15

Thr Ala Tyr Trp Lys Glu Leu Ser Leu Lys Tyr Lys Gln Ser Phe
                20                  25                  30

Gln Glu Ala Arg Asp Glu Leu Val Glu Phe Gln Glu Gly Ser Arg
                35                  40                  45

Glu Leu Glu Ala Glu Leu Glu Ala Gln Leu Val Gln Ala Glu Gln
                50                  55                  60

Arg Asn Arg Asp Leu Gln Ala Asp Asn Gln Arg Leu Lys Tyr Glu
                65                  70                  75

Val Glu Ala Leu Lys Glu Lys Leu Glu His Gln Tyr Ala Gln Ser
                80                  85                  90
```

```
Tyr Lys Gln Val Ser Val Leu Glu Asp Asp Leu Ser Gln Thr Arg
             95                 100                 105
Ala Ile Lys Glu Gln Leu His Lys Tyr Val Arg Glu Leu Glu Gln
            110                 115                 120
Ala Asn Asp Asp Leu Glu Arg Ala Lys Arg Ala Thr Ile Val Ser
            125                 130                 135
Leu Glu Asp Phe Glu Gln Arg Leu Asn Gln Ala Ile Glu Arg Asn
            140                 145                 150
Ala Phe Leu Glu Ser Glu Leu Asp Glu Lys Glu Ser Leu Leu Val
            155                 160                 165
Ser Val Gln Arg Leu Lys Asp Glu Ala Arg Asp Leu Arg Gln Glu
            170                 175                 180
Leu Ala Val Arg Glu Arg Gln Gln Glu Val Thr Arg Lys Ser Ala
            185                 190                 195
Pro Ser Ser Pro Thr Leu Asp Cys Glu Lys Met Asp Ser Ala Val
            200                 205                 210
Gln Ala Ser Leu Ser Leu Pro Ala Thr Pro Val Gly Lys Gly Thr
            215                 220                 225
Glu Asn Thr Phe Pro Ser Pro Lys Ala Ile Pro Asn Gly Phe Gly
            230                 235                 240
Thr Ser Pro Leu Thr Pro Ser Ala Arg Ile Ser Ala Leu Asn Ile
            245                 250                 255
Val Gly Asp Leu Leu Arg Lys Val Gly Ala Leu Glu Ser Lys Leu
            260                 265                 270
Ala Ala Cys Arg Asn Phe Ala Lys Asp Gln Ala Ser Arg Lys Ser
            275                 280                 285
Tyr Ile Ser Gly Asn Val Asn Cys Gly Val Leu Asn Gly Asn Gly
            290                 295                 300
Thr Lys Phe Ser Arg Ser Gly His Thr Ser Phe Phe Asp Lys Gly
            305                 310                 315
Ala Val Asn Gly Phe Asp Pro Ala Pro Pro Pro Gly Leu Gly
            320                 325                 330
Ser Ser Arg Pro Ser Ser Ala Pro Gly Met Leu Pro Leu Ser Val
            335                 340                 345
Arg Val Pro Ser Leu Gln Val Gly Ala Pro Ala Leu Leu Gln Gln
            350                 355                 360
Pro Arg Thr Pro Thr Pro His Pro Ser Val Pro Gly Pro Ser Pro
            365                 370                 375
Val Pro Leu Arg Leu Pro Pro His Gly Trp Gln Arg Ala Gly Cys
            380                 385                 390
Met Gln Trp Arg Leu Leu Gly Pro Ala Gln Pro Arg Asn Ser Ala
            395                 400                 405
Arg Tyr Gln Tyr Trp Leu Phe Ser Leu Leu Ala Val Val Pro Leu
            410                 415                 420
Val Ser His Asp Cys Thr Phe Val Gly Arg Lys Val Ile His Thr
            425                 430                 435
Cys Ile Thr Trp Ser Leu Asp Ala Glu Val Pro Ile His His Thr
            440                 445                 450
Cys Pro Ile Ala Pro Thr Leu Leu Tyr
            455

(2) INFORMATION FOR SEQ ID NO:     2:
```

(i) SEQUENCE CHARACTERISTICS:
    (A) LENGTH: 348 amino acids
    (B) TYPE: amino acid
    (C) STRANDEDNESS: single
    (D) TOPOLOGY: linear (vii) IMMEDIATE SOURCE:
    (A) LIBRARY: BLADNOT04
    (B) CLONE: 1319265

(xi) SEQUENCE DESCRIPTION: SEQ ID NO: 2 :

```
Met Trp Lys Thr Gln Ile Gly Ala Tyr Cys Gly Val Thr Thr Asp
              5                  10                  15

Val Arg Val Glu Arg Lys Asp Pro Asn Gln Val Glu Leu Trp Gly
             20                  25                  30

Leu Lys Glu Gly Thr Tyr Leu Phe Gln Leu Thr Val Thr Ser Ser
             35                  40                  45

Asp His Pro Glu Asp Thr Ala Asn Val Thr Val Thr Val Leu Ser
             50                  55                  60

Thr Lys Gln Thr Glu Asp Tyr Cys Leu Ala Ser Asn Lys Val Gly
             65                  70                  75

Arg Arg Cys Arg Gly Ser Phe Pro Arg Trp Tyr Tyr Asp Pro Thr
             80                  85                  90

Glu Gln Ile Cys Lys Ser Phe Val Tyr Gly Gly Cys Leu Gly Asn
             95                 100                 105

Lys Asn Asn Tyr Leu Arg Glu Glu Cys Ile Leu Ala Cys Arg
            110                 115                 120

Gly Val Gln Gly Gly Pro Leu Arg Gly Ser Ser Gly Ala Gln Ala
            125                 130                 135

Thr Phe Pro Gln Gly Pro Ser Met Glu Arg Arg His Pro Val Cys
            140                 145                 150

Ser Gly Thr Cys Gln Pro Thr Gln Phe Arg Cys Ser Asn Gly Cys
            155                 160                 165

Cys Ile Asp Ser Phe Leu Glu Cys Asp Asp Thr Pro Asn Cys Pro
            170                 175                 180

Asp Ala Ser Asp Glu Ala Ala Cys Glu Lys Tyr Thr Ser Gly Phe
            185                 190                 195

Asp Glu Leu Gln Arg Ile His Phe Pro Ser Asp Lys Gly His Cys
            200                 205                 210

Val Asp Leu Pro Asp Thr Gly Leu Cys Lys Glu Ser Ile Pro Arg
            215                 220                 225

Trp Tyr Tyr Asn Pro Phe Ser Glu His Cys Ala Arg Phe Thr Tyr
            230                 235                 240

Gly Gly Cys Tyr Gly Asn Lys Asn Asn Phe Glu Glu Glu Gln Gln
            245                 250                 255

Cys Leu Glu Ser Cys Arg Gly Ile Ser Lys Lys Asp Val Phe Gly
            260                 265                 270

Leu Arg Arg Glu Ile Pro Ile Pro Ser Thr Gly Ser Val Glu Met
            275                 280                 285

Ala Val Ala Val Phe Leu Val Ile Cys Ile Val Val Val Val Ala
            290                 295                 300

Ile Leu Gly Tyr Cys Phe Phe Lys Asn Gln Arg Lys Asp Phe His
            305                 310                 315

Gly His His His His Pro Pro Pro Thr Pro Ala Ser Ser Thr Val
            320                 325                 330

Ser Thr Thr Glu Asp Thr Glu His Leu Val Tyr Asn His Thr Thr
```

335                 340                 345
Arg Pro Leu (2) INFORMATION FOR SEQ ID NO:    3:

(i) SEQUENCE CHARACTERISTICS:
        (A) LENGTH: 238 amino acids
        (B) TYPE: amino acid
        (C) STRANDEDNESS: single
        (D) TOPOLOGY: linear (vii) IMMEDIATE SOURCE:
        (A) LIBRARY: BEPINOT01
        (B) CLONE: 2057812

(xi) SEQUENCE DESCRIPTION: SEQ ID NO: 3 :

Met Ser Asp Glu Glu Ala Arg Gln Ser Gly Gly Ser Ser Gln Ala
                  5                  10                  15

Gly Ala Val Thr Val Ser Asp Val Gln Glu Leu Met Arg Arg Lys
                 20                  25                  30

Glu Glu Ile Glu Ala Gln Ile Lys Ala Asn Tyr Asp Val Leu Glu
                 35                  40                  45

Ser Gln Lys Gly Ile Gly Met Asn Glu Pro Leu Val Asp Cys Glu
                 50                  55                  60

Gly Tyr Pro Arg Ser Asp Val Asp Leu Tyr Gln Val Arg Thr Ala
                 65                  70                  75

Arg His Asn Ile Ile Cys Leu Gln Asn Asp His Lys Ala Val Met
                 80                  85                  90

Lys Gln Val Glu Glu Ala Leu His Gln Leu His Ala Arg Asp Lys
                 95                 100                 105

Glu Lys Gln Ala Arg Asp Met Ala Glu Ala His Lys Glu Ala Met
                110                 115                 120

Ser Arg Lys Leu Gly Gln Ser Glu Ser Gln Gly Pro Pro Arg Ala
                125                 130                 135

Phe Ala Lys Val Asn Ser Ile Ser Pro Gly Ser Pro Ala Ser Ile
                140                 145                 150

Ala Gly Asn Pro Gly Val Gly His Ser Ser Pro Cys Pro Gly Asp
                155                 160                 165

Thr Gly Leu Gln Val Asp Asp Glu Ile Val Glu Phe Gly Ser Val
                170                 175                 180

Asn Thr Gln Asn Phe Gln Ser Leu His Asn Ile Gly Ser Val Val
                185                 190                 195

Gln His Ser Glu Gly Lys Pro Leu Asn Val Thr Val Ile Arg Arg
                200                 205                 210

Gly Gly Lys His Gln Leu Arg Leu Val Pro Thr Arg Trp Ala Gly
                215                 220                 225

Lys Gly Leu Leu Gly Cys Asn Ile Ile Pro Leu Gln Arg
                230                 235

(2) INFORMATION FOR SEQ ID NO:    4:

(i) SEQUENCE CHARACTERISTICS:
        (A) LENGTH: 471 amino acids
        (B) TYPE: amino acid
        (C) STRANDEDNESS: single
        (D) TOPOLOGY: linear (vii) IMMEDIATE SOURCE:
        (A) LIBRARY: OVARNOT03
        (B) CLONE: 2058485

(xi) SEQUENCE DESCRIPTION: SEQ ID NO: 4 :

```
Met Asn Gly Lys Ala Arg Lys Glu Ala Val Gln Thr Ala Ala Lys
                  5                  10                  15

Glu Leu Leu Lys Phe Val Asn Arg Ser Pro Ser Pro Phe His Ala
                 20                  25                  30

Val Ala Glu Cys Arg Asn Arg Leu Leu Gln Ala Gly Phe Ser Glu
                 35                  40                  45

Leu Lys Glu Thr Glu Lys Trp Asn Ile Lys Pro Glu Ser Lys Tyr
                 50                  55                  60

Phe Met Thr Arg Asn Ser Ser Thr Ile Ile Ala Phe Ala Val Gly
                 65                  70                  75

Gly Gln Tyr Val Pro Gly Asn Gly Phe Ser Leu Ile Gly Ala His
                 80                  85                  90

Thr Asp Ser Pro Cys Leu Arg Val Lys Arg Ser Arg Arg Ser
                 95                 100                 105

Gln Val Gly Phe Gln Gln Val Gly Val Glu Thr Tyr Gly Gly Gly
                110                 115                 120

Ile Trp Ser Thr Trp Phe Asp Arg Asp Leu Thr Leu Ala Gly Arg
                125                 130                 135

Val Ile Val Lys Cys Pro Thr Ser Gly Arg Leu Glu Gln Gln Leu
                140                 145                 150

Val His Val Glu Arg Pro Ile Leu Arg Ile Pro His Leu Ala Ile
                155                 160                 165

His Leu Gln Arg Asn Ile Asn Glu Asn Phe Gly Pro Asn Thr Glu
                170                 175                 180

Met His Leu Val Pro Ile Leu Ala Thr Ala Ile Gln Glu Glu Leu
                185                 190                 195

Glu Lys Gly Thr Pro Glu Pro Gly Pro Leu Asn Ala Val Asp Glu
                200                 205                 210

Arg His His Ser Val Leu Met Ser Leu Leu Cys Ala His Leu Gly
                215                 220                 225

Leu Ser Pro Lys Asp Ile Val Glu Met Glu Leu Cys Leu Ala Asp
                230                 235                 240

Thr Gln Pro Ala Val Leu Gly Gly Ala Tyr Asp Glu Phe Ile Phe
                245                 250                 255

Ala Pro Arg Leu Asp Asn Leu His Ser Cys Phe Cys Ala Leu Gln
                260                 265                 270

Ala Leu Ile Asp Ser Cys Ala Gly Pro Gly Ser Leu Ala Thr Glu
                275                 280                 285

Pro His Val Arg Met Val Thr Leu Tyr Asp Asn Glu Glu Val Gly
                290                 295                 300

Ser Glu Ser Ala Gln Gly Ala Gln Ser Leu Leu Thr Glu Leu Val
                305                 310                 315

Leu Arg Arg Ile Ser Ala Ser Cys Gln His Pro Thr Ala Phe Glu
                320                 325                 330

Glu Ala Ile Pro Lys Ser Phe Met Ile Ser Ala Asp Met Ala His
                335                 340                 345

Ala Val His Pro Asn Tyr Leu Asp Lys His Glu Glu Asn His Arg
                350                 355                 360

Pro Leu Phe His Lys Gly Pro Val Ile Lys Val Asn Ser Lys Gln
                365                 370                 375

Arg Tyr Ala Ser Asn Ala Val Ser Glu Ala Leu Ile Arg Glu Val
```

-continued

```
                380               385               390
Ala Asn Lys Val Lys Val Pro Leu Gln Asp Leu Met Val Arg Asn
                     395               400               405
Asp Thr Pro Cys Gly Thr Thr Ile Gly Pro Ile Leu Ala Ser Arg
                410               415               420
Leu Gly Leu Arg Val Leu Asp Leu Gly Ser Pro Gln Leu Ala Met
                425               430               435
His Ser Ile Arg Glu Met Ala Cys Thr Thr Gly Val Leu Gln Thr
                440               445               450
Leu Thr Leu Phe Lys Gly Phe Phe Glu Leu Phe Pro Ser Leu Ser
                     455               460               465
His Asn Leu Leu Val Asp
                470
```

(2) INFORMATION FOR SEQ ID NO: 5:

(i) SEQUENCE CHARACTERISTICS:
        (A) LENGTH: 2327 base pairs
        (B) TYPE: nucleic acid
        (C) STRANDEDNESS: single
        (D) TOPOLOGY: linear (vii) IMMEDIATE SOURCE:
        (A) LIBRARY: THP1NOB01
        (B) CLONE: 031381

(xi) SEQUENCE DESCRIPTION: SEQ ID NO: 5 :

```
CGGGCGCGGA GGTACGCTGA GTGGAGCTCG GGCTGCGTA GGGGAGCTGA GCCGAGCGGC    60
TGGGCGGGCC TGGCCGGGCC AGCGGAGGGG AGACGTCGGT TGAGCGGCGG CGAACATGCG   120
CTTTTGACAC ATTGGAGGCT TCTTGATCA TGGATGGTGA AGATATACCA GATTTTTCAA   180
GTTTAAAGGA GGAAACTGCT TATTGGAAGG AACTTTCCTT GAAGTATAAG CAAAGCTTCC   240
AGGAAGCTCG GGATGAGCTA GTTGAATTCC AGGAAGGAAG CAGAGAATTA AAGCAGAGT    300
TGGAGGCACA ATTAGTACAG GCTGAACAAA GAAATAGAGA CTTGCAGGCT GATAACCAAA   360
GACTGAAATA TGAAGTGGAG GCATTAAAGG AGAAGCTAGA GCATCAATAT GCACAGAGCT   420
ATAAGCAGGT CTCAGTGTTA GAAGATGATT TAAGTCAGAC TCGGGCCATT AAGGAGCAGT   480
TGCATAAGTA TGTGAGAGAG CTGGAGCAGG CCAACGACGA CCTGGAGCGA GCCAAAAGGG   540
CAACAATAGT TTCACTGGAA GACTTTGAAC AAAGGCTAAA CCAGGCCATT GAACGAAATG   600
CATTTTTAGA AAGTGAACTT GATGAAAAGG AATCTTTGTT GGTCTCTGTA CAGAGGTTAA   660
AGGATGAAGC AAGAGATTTA AGGCAAGAAC TAGCAGTTCG GGAAAGACAA CAGGAAGTAA   720
CTAGAAAGTC GGCTCCTAGC TCTCCAACTC TAGACTGTGA AAAGATGGAC TCCGCCGTCC   780
AAGCATCACT TTCTTTGCCA GCTACCCCTG TTGGCAAAGG AACGGAGAAC ACTTTTCCTT   840
CACCGAAAGC TATACCAAAT GGTTTTGGTA CCAGTCCACT AACTCCCTCT GCTAGGATAT   900
CAGCACTAAA CATCGTGGGG GATCTCTTAC GGAAAGTAGG GGCTTTAGAA TCCAAATTAG   960
CAGCTTGCAG GAATTTTGCA AAGGACCAAG CATCACGAAA ATCCTATATT TCAGGGAATG  1020
TTAACTGTGG GGTGCTGAAT GGCAATGGCA CAAAGTTCTC TCGATCAGGG CATACATCTT  1080
TCTTCGACAA AGGGGCAGTA AACGGCTTTG ACCCCGCTCC TCCTCCTCCT GGTCTGGGCT  1140
CCTCGCGTCC ATCGTCAGCG CCGGGTATGC TGCCTCTCAG TGTGCGAGTG CCTAGCCTCC  1200
AGGTGGGGGC TCCTGCCCTC CTCCAACAAC CCAGGACACC CACGCCTCAC CCCTCGGTGC  1260
CTGGGCCCAG CCCCGTGCCC CTCCGTCTGC CTCCGCACGG CTGGCAGAGG GCAGGCTGCA  1320
```

```
TGCAGTGGCG GCTACTGGGC CCTGCCCAGC CCCGGAACTC TGCGCGATAT CAATACTGGC      1380

TATTTTCTCT TCTCGCCGTA GTGCCGTTGG TTTCACATGA TTGCACTTTT GTGGGTCGCA      1440

AGGTGATACA TACGTGTATT ACTTGGTCAC TGGATGCAGA AGTACCCATT CATCACACCT      1500

GCCCCATAGC CCCCACTCTG CTGTACTGAT AGGATTTAGT TGTGTTTTAG GACATTGCAA      1560

ATCTTCTAGA AGTTCTCCCC CAAATCAGGT CAATGTGTGC CCTCCTGAGC TCCCACCCAG      1620

GCATCTCCAG TGCTCATGAT CATGTGTCCC CCAACTCCAC CCCTCACAGT TGGGCCTGT       1680

TTCTGGCAAA GAGTCAGGAA GGTTACTGAA TTAGGGAACA TTTTCTGCAC CTTCTGATTT      1740

TACTTAAGCA GCTACCATTC CATGGACTTG CCTCCCAGAG CAGCACAATG CCCGTCTGAG      1800

CCCCACGTGG CAGGAGCCTC TGGGACGGGG CACACACAGG CCCAGCCTCT GTGCTGTCTC      1860

CTCCTCTGTG CGCCTCAGAC TCGGGGTGAG GGAGGCGGGC AGCCTCTCGC CAGCCTTCCC      1920

GTCCTTCAGT TCAACGACAT CTTTGGAGTG TTTTTGTTTT CTCTTCCAAG GGCCGTCCCG      1980

TTGTGTTAGG AAGGGTGAGT GGCTGGTTCC AGGGTGGGCC GGTGCCAGCT CCGGGGTGGA      2040

CTGAACAGCG GCGGCTGTCC CTGTGCATCC TTTGATTACT CTCATGCTGC ATTTACTGTT      2100

TACATTTGTT TTATTGTACA TAGGTTTGTA AACATTATTG CCTGAGATAT TTGTATATAA      2160

CTTGGGCTTT GTAGCTTTTA TTTATTCAGA ACGCATACGG CATGTTAATG ACTCTGATGG      2220

TGTCCTCCTC TGGGCAGCTG TATAGGATCA TCATGTGGTT ACAAAAAATA CTTCCCTCAA      2280

AAAAATTCTT TTAATGTGGA AACAATAAAT TTCACAGAAA AAAAAA                     2327

(2) INFORMATION FOR SEQ ID NO:    6:

(i) SEQUENCE CHARACTERISTICS:
         (A) LENGTH: 1870 base pairs
         (B) TYPE: nucleic acid
         (C) STRANDEDNESS: single
         (D) TOPOLOGY: linear (vii) IMMEDIATE SOURCE:
         (A) LIBRARY: BLADNOT04
         (B) CLONE: 1319265

(xi) SEQUENCE DESCRIPTION: SEQ ID NO: 6 :

CTGAGAGAAG CCTGGTCCAT CTAGTGAGAA TTGACCTTAT CTCACTTTCT CTCCCCGCCA        60

GGGTCTGGGA TCCCCAAGGC CTGGGCAGGC ATAGACTTGA AGGTACAACC CCAGGAACCC       120

CTGGTGCTGA AGGATGTGGA AAACACAGAT TGGCGCCTAC TGCGGGGTGA CAACGGATGT       180

CAGGGTAGAG AGGAAAGACC CAAACCAGGT GGAACTGTGG GGACTCAAGG AAGGCACCTA       240

CCTGTTCCAG CTGACAGTGA CTAGCTCAGA CCACCCAGAG GACACGGCCA ACGTCACAGT       300

CACTGTGCTG TCCACCAAGC AGACAGAAGA CTACTGCCTC GCATCCAACA AGGTGGGTCG       360

CCGCTGCCGG GGCTCTTTCC CGCGCTGGTA CTATGACCCC ACGGAGCAGA TCTGCAAGAG       420

TTTCGTTTAT GGAGGCTGCT TGGGCAACAA GAACAACTAC CTTCGGGAAG AAGAGTGCAT       480

TCTAGCCTGT CGGGGTGTGC AAGGTGGGCC TTTGAGAGGC AGCTCTGGGG CTCAGGCGAC       540

TTTCCCCCAG GGCCCCTCCA TGGAAAGGCG CCATCCAGTG TGCTCTGGCA CCTGTCAGCC       600

CACCCAGTTC CGCTGCAGCA ATGGCTGCTG CATCGACAGT TTCCTGGAGT GTGACGACAC       660

CCCCAACTGC CCCGACGCCT CCGACGAGGC TGCCTGTGAA AAATACACGA GTGGCTTTGA       720

CGAGCTCCAG CGCATCCATT TCCCCAGTGA CAAAGGGCAC TGCGTGGACC TGCCAGACAC       780

AGGACTCTGC AAGGAGAGCA TCCCGCGCTG GTACTACAAC CCCTTCAGCG AACACTGCGC       840

CCGCTTTACC TATGGTGGTT GTTATGGCAA CAAGAACAAC TTTGAGGAAG AGCAGCAGTG       900
```

```
CCTCGAGTCT TGTCGCGGCA TCTCCAAGAA GGATGTGTTT GGCCTGAGGC GGGAAATCCC      960

CATTCCCAGC ACAGGCTCTG TGGAGATGGC TGTCGCAGTG TTCCTGGTCA TCTGCATTGT     1020

GGTGGTGGTA GCCATCTTGG GTTACTGCTT CTTCAAGAAC CAGAGAAAGG ACTTCCACGG     1080

ACACCACCAC CACCCACCAC CCACCCCTGC CAGCTCCACT GTCTCCACTA CCGAGGACAC     1140

GGAGCACCTG GTCTATAACC ACACCACCCG GCCCCTCTGA GCCTGGGTCT CACCGGCTCT     1200

CACCTGGCCC TGCTTCCTGC TTGCCAAGGC AGAGGCCTGG GCTGGGAAAA ACTTTGGAAC     1260

CAGACTCTTG CCTGTTTCCC AGGCCCACTG TGCCTCAGAG ACCAGGGCTC CAGCCCCTCT     1320

TGGAGAAGTC TCAGCTAAGC TCACGTCCTG AGAAAGCTCA AAGGTTTGGA AGGAGCAGAA     1380

AACCCTTGGG CCAGAAGTAC CAGACTAGAT GGACCTGCCT GCATAGGAGT TTGGAGGAAG     1440

TTGGAGTTTT GTTTCCTCTG TTCAAAGCTG CCTGTCCCTA CCCCATGGTG CTAGGAAGAG     1500

GAGTGGGGTG GTGTCAGACC CTGGAGGCCC AACCCTGTC CTCCCGAGCT CCTCTTCCAT     1560

GCTGTGCGCC CAGGGCTGGG AGGAAGGACT TCCCTGTGTA GTTTGTGCTG TAAAGAGTTG     1620

CTTTTTGTTT ATTTAATGCT GTGGCATGGG TGAAGAGGAG GGGAAGAGGC CTGTTTGGCC     1680

TCTCTGTCCT CTCTTCCTCT TCCCCCAAGA TTGAGCTCTC TGCCCTTGAT CAGCCCCACC     1740

CTGGCCTAGA CCAGCAGACA GAGCCAGGAG AGGCTCAGCT GCATTCCGCA GCCCCCACCC     1800

CCAAGGTTCT CCAACATCAC AGCCCAGCCC ACCCACTGGG TAATAAAAGT GGTTTGTGGA     1860

AAAAAAAAA                                                             1870

(2) INFORMATION FOR SEQ ID NO:   7:

(i) SEQUENCE CHARACTERISTICS:
        (A) LENGTH: 1138 base pairs
        (B) TYPE: nucleic acid
        (C) STRANDEDNESS: single
        (D) TOPOLOGY: linear (vii) IMMEDIATE SOURCE:
        (A) LIBRARY: BEPINOT01
        (B) CLONE: 2057812

(xi) SEQUENCE DESCRIPTION: SEQ ID NO: 7 :

GTTTTGGCGC ATGGGCGGAG CGTAGTTACG GTCGACTGGG GCGTCGTCCC TAGCCCGGGA       60

GCCGGGTCTC TGGAGTCGCG GCCCGGGGTT CACGATGTCC GACGAGGAAG CGAGGCAGAG      120

CGGAGGCTCC TCGCAGGCCG GCGCCGTGAC TGTCAGCGAC GTCCAGGAGC TGATGCGGCG      180

CAAGGAGGAG ATAGAAGCGC AGATCAAGGC CAACTATGAC GTGCTGGAAA GCCAAAAAGG      240

CATTGGGATG AACGAGCCGC TGGTGGACTG TGAGGGCTAC CCCCGGTCAG ACGTGGACCT      300

GTACCAAGTC CGCACCGCCA GGCACAACAT CATATGCCTG CAGAATGATC ACAAGGCAGT      360

GATGAAGCAG GTGGAGGAGG CCCTGCACCA GCTGCACGCT CGCGACAAGG AGAAGCAGGC      420

CCGGGACATG GCTGAGGCCC ACAAAGAGGC CATGAGCCGC AAACTGGGTC AGAGTGAGAG      480

CCAGGGCCCT CCACGGGCCT TCGCCAAAGT GAACAGCATC AGCCCCGGCT CCCCAGCCAG      540

CATCGCGGGT AATCCAGGGG TTGGCCACTC AAGTCCATGC CAGGGGACA CGGGTCTGCA      600

AGTGGATGAT GAGATTGTGG AGTTCGGCTC TGTGAACACC CAGAACTTCC AGTCACTGCA      660

TAACATTGGC AGTGTGGTGC AGCACAGTGA GGGGAAGCCC CTGAATGTGA CAGTGATCCG      720

CAGGGGGGGA AAACACCAGC TTAGACTTGT TCCAACACGC TGGGCAGGAA AAGGACTGCT      780

GGGCTGCAAC ATTATTCCTC TGCAAAGATG ATTGTCCCTG GGAACAGTA ACAGGAAAGC      840

ATCTTCCCTT GCCCTGGACT TGGGTCTAGG GATTTCCAAC TTGTCTTCTC TCCCTGAAGC      900
```

```
ATAAGGATCT GGAAGAGGCT TGTAACCTGA ACTTCTGTGT GGTGGCAGTA CTGTGGCCCA    960

CCAGTGTAAT CTCCCTGGAT TAAGGCATTC TTAAAAACTT AGGCTTGGCC TCTTTCACAA   1020

ATTAGGCCAC GGCCCTAAAT AGGAATTCCC TGGATTGTGG GCAAGTGGGC GGAAGTTATT   1080

CTGGCAGGTA CTGGTGTGAT TATTATTATT ATTTTTAATA AAGAGTTTTA CAGTGCTG    1138
```

(2) INFORMATION FOR SEQ ID NO:    8:

(i) SEQUENCE CHARACTERISTICS:
        (A) LENGTH: 1910 base pairs
        (B) TYPE: nucleic acid
        (C) STRANDEDNESS: single
        (D) TOPOLOGY: linear (vii) IMMEDIATE SOURCE:
        (A) LIBRARY: OVARNOT03
        (B) CLONE: 2058485

(xi) SEQUENCE DESCRIPTION: SEQ ID NO: 8 :

```
CGAGCCCGGA GGCCAGATGA GCGGACACAG CCCCACGCGC GGGGCCATGC AGGTAAGTGG     60

CTCCCGACGG CCCCACTTGA ATTTCGATCC CAGACCGGGT CCGGCGCCCT CCGGGGCCCA    120

AGCTTAGCGC GGTGCTGCAG TGGGGCCGCC TGACCCAAAG CGAAACCGAA AGCCCCGCGG    180

AGGGTGACCT GACGACTTTC CCGGGACTGG AAGGGGGAGT CCTGCGAGAG ACTAGGTGGC    240

CATGAACGGT AAGGCCCGCA AGAGGCGGT GCAGACTGCG GCTAAGGAAC TCCTCAAGTT     300

CGTGAACCGG AGTCCCTCTC CTTTCCATGC TGTGGCTGAA TGCCGCAACC GCCTTCTCCA    360

GGCTGGCTTC AGTGAACTCA AGGAGACTGA GAAATGGAAT ATTAAGCCCG AGAGCAAGTA    420

CTTCATGACC AGGAACTCCT CCACCATCAT AGCTTTTGCT GTAGGGGCC AGTACGTTCC     480

TGGCAATGGC TTCAGCCTCA TCGGGCCCA CACGGACAGC CCCTGCCTCC GGGTGAAACG     540

TCGGTCTCGC CGCAGCCAGG TGGGCTTCCA GCAAGTCGGT GTGGAGACCT ATGGTGGTGG    600

GATCTGGAGC ACCTGGTTTG ACCGTGACCT GACTCTGGCT GGACGCGTCA TTGTCAAGTG    660

CCCTACCTCA GGTCGGCTGG AGCAGCAGCT GGTGCACGTG GAGCGGCCCA TTCTTCGCAT    720

CCCACACCTG GCCATCCATC TGCAGCGAAA TATCAACGAG AACTTTGGGC CAACACAGA     780

GATGCATCTA GTCCCCATTC TTGCCACAGC CATCCAGGAG GAGCTGGAGA AGGGGACTCC    840

TGAGCCAGGG CCTCTCAATG CTGTGGATGA GCGGCACCAT TCGGTCCTCA TGTCCCTGCT    900

CTGTGCCCAT CTGGGGCTGA GCCCCAAGGA CATAGTGGAG ATGGAGCTCT GCCTTGCAGA    960

CACCCAGCCT GCGGTCTTGG GTGGTGCCTA TGATGAGTTC ATCTTTGCTC CTCGGCTGGA   1020

CAATCTGCAC AGCTGCTTCT GTGCCCTGCA GGCCTTGATA GATTCCTGTG CAGGCCCTGG   1080

CTCCCTGGCC ACAGAGCCTC ACGTGCGCAT GGTCACACTC TATGACAACG AAGAGGTGGG   1140

GTCTGAGAGT GCACAGGGAG CACAGTCACT GCTGACAGAG CTGGTGCTGC GGCGGATCTC   1200

AGCCTCGTGC CAGCACCCGA CAGCCTTCGA GGAAGCCATA CCCAAGTCCT TCATGATCAG   1260

CGCAGACATG GCCCATGCTG TGCATCCCAA CTACCTGGAC AAGCATGAGG AGAACCACCG   1320

GCCTTTATTC CACAAGGGCC CCGTGATCAA GGTGAACAGC AAGCAACGCT ATGCTTCAAA   1380

CGCGGTGTCA GAGGCCCTGA TCCGAGAGGT GGCCAACAAA GTCAAGGTCC CCTGCAGGA    1440

TCTCATGGTC CGGAATGACA CCCCCTGTGG AACCACCATT GGACCTATCT TGGCTTCTCG   1500

GCTGGGGCTG CGGGTGCTGG ATTTAGGCAG CCCCCAACTG GCCATGCACT CTATCCGGGA   1560

GATGGCCTGC ACCACAGGAG TCCTCCAGAC CCTCACCCTC TTCAAGGGCT TCTTTGAGCT   1620

GTTCCCTTCT CTAAGCCATA ATCTCTTAGT GGATTGAGCC CTCTTGGAAA GACTTCTCTG   1680
```

```
CCATCCCTTT GCACCTGAGA GGGGAAGTTC TCAGCTGAGC TGAAGCTGGA TTATTAAAGT    1740

GGATTGTCAC TCAGACTCTC CGTGCTACGC TTATTTGGAG ACTAGAGGAG TGGGAGTTGA    1800

GCCTGGCTTG AACCTTTGGA ACCAGAAAAG TTGGGGAGCA GGTGGAGGAG GCCACACTCC    1860

TGGGAGCTGA TGGTTTTAAA TCTGGTTTTA AATCTCAAAA AAAAAAAAA                1910
```

(2) INFORMATION FOR SEQ ID NO:9:

(i) SEQUENCE CHARACTERISTICS:
        (A) LENGTH: 667 amino acids
        (B) TYPE: amino acid
        (C) STRANDEDNESS: single
        (D) TOPOLOGY: linear (xi) SEQUENCE DESCRIPTION: SEQ ID NO:9:

```
Lys Pro Ala Cys Ser Ser Val Arg Leu Thr Thr Arg Glu Lys Pro His
  1               5                  10                  15

Cys Val Cys Gln Asp Pro Met Thr Cys Pro Ala Lys Leu Leu Asp
             20                  25                  30

Gln Val Cys Gly Thr Asp Asn Gln Thr Tyr Thr Ser Ser Cys Tyr Leu
             35                  40                  45

Phe Ala Thr Lys Cys Lys Leu Glu Gly Thr Lys Lys Gly His Gln Leu
 50                  55                  60

Gln Leu Ile Thr Trp Ser Leu Gln Ile Tyr Pro Ala Cys Thr Asp Phe
 65                  70                  75                  80

Glu Val Thr Gln Phe Pro Leu Arg Met Arg Asp Trp Leu Lys Asn Ile
                 85                  90                  95

Ser Cys Ser Cys Met Asn Leu Thr Leu Asn Thr Leu Asp Ile Ser Thr
                100                 105                 110

Arg Ser Arg Glu Thr Lys Ser Arg Lys Ser Thr Trp Met Lys Lys Arg
            115                 120                 125

Leu Leu Ala Gly Asp His Pro Ile Asp Leu Leu Arg Glu His Arg
130                 135                 140

Ala Thr Ser Arg Phe Gly Gln Val Arg Gln Leu Leu Thr Cys Arg Gly
145                 150                 155                 160

Gly Ala Gly Cys Arg Gly Ala Arg Ser Gly Ala Gln Gly Cys Gly Gly
                165                 170                 175

Asn Gly Ala Glu Arg Leu Gly Arg Pro Gly Gln Ala Ser Gly Ala Glu
            180                 185                 190

Ala Ser Val Ser Arg Arg Arg Thr Cys Ala Phe Asp Thr Leu Glu Ala
            195                 200                 205

Phe Leu Ile Met Asp Gly Glu Asp Ile Pro Asp Phe Ser Ser Leu Lys
210                 215                 220

Glu Glu Thr Ala Tyr Trp Lys Glu Leu Ser Leu Lys Tyr Lys Gln Ser
225                 230                 235                 240

Ser Arg Lys Ala Arg Asp Glu Leu Val Glu Phe Gln Glu Gly Ser Arg
                245                 250                 255

Glu Leu Glu Ala Glu Leu Glu Ala Gln Leu Val Gln Ala Glu Gln Arg
            260                 265                 270

Asn Arg Asp Leu Gln Ala Asp Asn Gln Arg Leu Lys Tyr Glu Val Glu
            275                 280                 285

Ala Leu Lys Glu Lys Leu Glu His Gln Tyr Ala Gln Ser Tyr Lys Gln
290                 295                 300

Val Ser Val Leu Glu Asp Asp Leu Ser Gln Thr Arg Ala Ile Lys Glu
305                 310                 315                 320
```

```
Gln Leu His Ser Thr Cys Arg Glu Leu Glu Gln Ala Asn Asp Asp Leu
                325                 330                 335

Glu Arg Ala Lys Arg Ala Thr Ile Val Ser Leu Glu Thr Leu Thr Lys
            340                 345                 350

Leu Asn Gln Ala Ile Glu Arg Asn Ala Phe Leu Glu Ser Glu Leu Asp
        355                 360                 365

Glu Lys Glu Ser Leu Leu Val Ser Val Gln Arg Leu Lys Asp Glu Ala
    370                 375                 380

Arg Asp Leu Arg Gln Glu Leu Ala Val Arg Glu Arg Gln Gln Glu Val
385                 390                 395                 400

Thr Arg Lys Ser Ala Pro Ser Ser Pro Thr Leu Asp Cys Glu Lys Met
                405                 410                 415

Asp Ser Ala Val Gln Ala Ser Leu Ser Leu Pro Ala Thr Pro Val Gly
                420                 425                 430

Lys Gly Thr Glu Asn Ser Phe Pro Ser Pro Lys Ala Ile Pro Asn Gly
            435                 440                 445

Phe Gly Thr Ser Pro Leu Thr Pro Ser Ala Arg Ile Ser Ala Leu Asn
        450                 455                 460

Ile Val Gly Asp Leu Leu Arg Lys Val Gly Ala Leu Glu Ser Lys Leu
465                 470                 475                 480

Ala Ala Cys Arg Asn Phe Ala Lys Asp Gln Ala Ser Arg Lys Ser Tyr
                485                 490                 495

Ile Ser Gly Asn Val Asn Cys Gly Val Met Asn Ser Asn Gly Thr Lys
            500                 505                 510

Phe Ser Arg Ser Gly His Thr Ser Phe Phe Asp Lys Gly Ala Val Asn
        515                 520                 525

Gly Phe Asp Pro Ala Pro Pro Pro Gly Leu Gly Ser Ser Arg Pro
    530                 535                 540

Leu Ser Ala Pro Gly Met Cys Arg Ser Val Cys Glu Cys Pro Ala Ser
545                 550                 555                 560

Gly Ala Pro Ala Leu Leu Gln Gln Pro Arg Thr Pro Thr Pro His Pro
                565                 570                 575

Ser Val Pro Gly Pro Ala Leu Cys Pro Pro Ser Ala Ser Pro His Gly
                580                 585                 590

Trp Gln Arg Ala Gly Cys Met Gln Trp Arg Cys Phe Gly Pro Ala Gln
            595                 600                 605

Pro Gln Asp Ser Ala Arg Tyr Gln Tyr Trp Leu Phe Ser Leu Leu Ala
        610                 615                 620

Val Val Pro Leu Val Ser His Asp Cys Thr Phe Val Gly His Glu Val
625                 630                 635                 640

Ile His Thr Cys Ile Thr Trp Ser Leu Asp Ala Glu Val Pro Ile Cys
                645                 650                 655

His Pro Cys Leu Ile Ala Pro Ala Leu Leu Tyr
                660                 665

(2) INFORMATION FOR SEQ ID NO:10:

(i) SEQUENCE CHARACTERISTICS:
        (A) LENGTH: 252 amino acids
        (B) TYPE: amino acid
        (C) STRANDEDNESS: single
        (D) TOPOLOGY: linear (xi) SEQUENCE DESCRIPTION: SEQ ID NO:10:

Met Ala Gln Leu Cys Gly Leu Arg Arg Ser Arg Ala Phe Leu Ala Leu
1               5                   10                  15
```

```
Leu Gly Ser Leu Leu Leu Ser Gly Val Leu Ala Ala Asp Arg Glu Arg
             20                  25                  30

Ser Ile His Asp Phe Cys Leu Val Ser Lys Val Val Gly Arg Cys Arg
         35                  40                  45

Ala Ser Met Pro Arg Trp Trp Tyr Asn Val Thr Asp Gly Ser Cys Gln
     50                  55                  60

Leu Phe Val Tyr Gly Gly Cys Asp Gly Asn Ser Asn Asn Tyr Leu Thr
 65                  70                  75                  80

Lys Glu Glu Cys Leu Lys Lys Cys Ala Thr Val Thr Glu Asn Ala Thr
                 85                  90                  95

Gly Asp Leu Ala Thr Ser Arg Asn Ala Ala Asp Ser Ser Val Pro Ser
                100                 105                 110

Ala Pro Arg Arg Gln Asp Ser Glu Asp His Ser Ser Asp Met Phe Asn
            115                 120                 125

Tyr Glu Glu Tyr Cys Thr Ala Asn Ala Val Thr Gly Pro Cys Arg Ala
        130                 135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
                165                 170                 175

Glu Ala Cys Met Leu Arg Cys Phe Arg Gln Glu Asn Pro Pro Leu
                180                 185                 190

Pro Leu Gly Ser Lys Val Val Leu Ala Gly Leu Phe Val Met Val
            195                 200                 205

Leu Ile Leu Phe Leu Gly Ala Ser Met Val Tyr Leu Ile Arg Val Ala
    210                 215                 220

Arg Arg Asn Gln Glu Arg Ala Leu Arg Thr Val Trp Ser Ser Gly Asp
225                 230                 235                 240

Asp Lys Glu Gln Leu Val Lys Asn Thr Tyr Val Leu
                245                 250

(2) INFORMATION FOR SEQ ID NO:11:

(i) SEQUENCE CHARACTERISTICS:
        (A) LENGTH: 209 amino acids
        (B) TYPE: amino acid
        (C) STRANDEDNESS: single
        (D) TOPOLOGY: linear (xi) SEQUENCE DESCRIPTION: SEQ ID NO:11:

Met Ser Asp Glu Glu Ala Arg Gln Ser Gly Gly Ser Ser Gln Ala Gly
 1               5                  10                  15

Val Val Thr Val Ser Asp Val Gln Glu Leu Met Arg Arg Lys Glu Glu
             20                  25                  30

Ile Glu Ala Gln Ile Lys Ala Asn Tyr Asp Val Leu Glu Ser Gln Lys
         35                  40                  45

Gly Ile Gly Met Asn Glu Pro Leu Val Asp Cys Glu Gly Tyr Pro Arg
     50                  55                  60

Ser Asp Val Asp Leu Tyr Gln Val Arg Thr Ala Arg His Asn Ile Ile
 65                  70                  75                  80

Cys Leu Gln Asn Asp His Lys Ala Val Met Lys Gln Val Glu Glu Ala
                 85                  90                  95

Leu His Gln Leu His Ala Arg Asp Lys Glu Lys Gln Ala Arg Asp Met
                100                 105                 110

Ala Glu Ala His Lys Glu Ala Met Ser Arg Lys Leu Gly Gln Ser Glu
```

```
                115                 120                 125
Ser Gln Gly Pro Pro Arg Ala Phe Ala Lys Val Asn Ser Ile Ser Pro
    130                 135                 140

Gly Ser Pro Ala Ser Ile Ala Gly Leu Gln Val Asp Asp Glu Ile Val
145                 150                 155                 160

Glu Phe Gly Ser Val Asn Thr Gln Asn Phe Gln Ser Leu His Asn Ile
                165                 170                 175

Gly Ser Val Val Gln His Ser Glu Gly Ala Leu Ala Pro Thr Ile Leu
            180                 185                 190

Leu Ser Val Ser Met Asn Leu Thr Thr Pro Gly Thr Ser Ser Arg Ser
        195                 200                 205

Pro (2) INFORMATION FOR SEQ ID NO:12:

(i) SEQUENCE CHARACTERISTICS:
        (A) LENGTH: 470 amino acids
        (B) TYPE: amino acid
        (C) STRANDEDNESS: single
        (D) TOPOLOGY: linear (xi) SEQUENCE DESCRIPTION: SEQ ID NO:12:

Met Ala Ala Ala Leu Lys Pro Ser Ala Pro Glu Ile Arg Lys Ala Ala
1               5                   10                  15

Gln Glu Phe Ile Asn Tyr Leu Asn Lys Ala Val Thr Pro Phe His Ala
            20                  25                  30

Thr Gln Glu Val Lys Asp Arg Leu Leu Gln Ala Gly Phe Thr Glu Leu
        35                  40                  45

Pro Glu Ser Gly His Trp Asp Ile Gln Pro Thr Ser Lys Tyr Phe Val
    50                  55                  60

Thr Lys Asn Arg Ser Ala Ile Leu Ala Phe Ala Val Gly Gly Ser Tyr
65                  70                  75                  80

Lys Pro Gly Ser Gly Phe Ser Ile Val Val Gly His Thr Asp Ser Pro
                85                  90                  95

Cys Leu Arg Val Lys Pro Ile Ser His Gln Lys Ser Asp Lys Phe Leu
            100                 105                 110

Gln Val Gly Val Ser Thr Tyr Gly Gly Gly Ile Trp Arg Thr Trp Phe
        115                 120                 125

Asp Arg Asp Leu Ser Val Ala Gly Leu Val Ile Val Lys Asn Gly Glu
    130                 135                 140

Lys Leu Gln His Lys Leu Ile Asp Val Lys Lys Pro Val Leu Phe Ile
145                 150                 155                 160

Pro Asn Leu Ala Ile His Leu Glu Thr Asp Arg Thr Thr Phe Lys Pro
                165                 170                 175

Asn Thr Glu Thr Glu Leu Arg Pro Ile Leu Glu Thr Phe Ala Ala Ala
            180                 185                 190

Gly Ile Asn Ala Pro Gln Lys Pro Glu Ser Thr Gly Phe Ala Asp Pro
        195                 200                 205

Arg Asn Ile Thr Asn Asn His His Pro Gln Phe Leu Gly Leu Ile Ala
    210                 215                 220

Lys Glu Ala Gly Cys Gln Pro Glu Asp Ile Val Asp Leu Asp Leu Tyr
225                 230                 235                 240

Leu Tyr Asp Thr Asn Lys Ala Ala Ile Val Gly Met Glu Asp Glu Phe
                245                 250                 255

Ile Ser Gly Ala Arg Leu Asp Asn Gln Val Gly Thr Tyr Thr Ala Ile
```

-continued

```
                     260                 265                 270
Ser Gly Leu Leu Glu Ser Leu Thr Gly Glu Ser Phe Lys Asn Asp Pro
            275                 280                 285
Gln Ile Arg Ile Ala Ala Cys Phe Asp Asn Glu Glu Val Gly Ser Asp
        290                 295                 300
Ser Ala Met Gly Ala Ser Ser Ser Phe Thr Glu Phe Val Leu Arg Arg
305                 310                 315                 320
Leu Ser Ala Gly Gly Ser Thr Thr Ala Phe Glu Glu Ala Ile Gly Lys
                325                 330                 335
Ser Met Leu Ile Ser Ala Asp Gln Ala His Ala Thr His Pro Asn Tyr
            340                 345                 350
Ser Ala Lys His Glu Glu Asn His Arg Pro Ala Phe His Gly Gly Val
            355                 360                 365
Val Val Lys Val Asn Val Asn Gln Arg Tyr Ala Thr Thr Ser Thr Thr
            370                 375                 380
His Ala Ala Leu Lys Gln Val Ala Phe Glu Ala Gln Val Pro Leu Gln
385                 390                 395                 400
Val Val Val Val Arg Asn Asp Ser Pro Cys Gly Ser Thr Val Gly Pro
                405                 410                 415
Ile Leu Ala Thr Lys Leu Gly Leu Gln Thr Val Asp Val Gly Cys Pro
                420                 425                 430
Gln Leu Ala Met His Ser Ile Arg Glu Phe Ala Asp Thr Ser Ser Ile
            435                 440                 445
Tyr Gln Ala Thr Thr Leu Tyr Ser Thr Phe Tyr Glu Arg Leu Ser Thr
        450                 455                 460
Val Leu Ser Asn Met Gln
465                 470
```